(12) United States Patent
Hadian et al.

(10) Patent No.: US 10,449,291 B2
(45) Date of Patent: Oct. 22, 2019

(54) PUMP CLIP FOR A FLUID INFUSION DEVICE

(71) Applicant: MEDTRONIC MINIMED, INC., Northridge, CA (US)

(72) Inventors: Ali Hadian, Granada Hills, CA (US); Shixin Chen, Simi Valley, CA (US); Chad A. Crane, Valencia, CA (US); Mitchell T. Johnson, Burbank, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 4 days.

(21) Appl. No.: 15/690,160

(22) Filed: Aug. 29, 2017

(65) Prior Publication Data

US 2018/0064868 A1    Mar. 8, 2018

Related U.S. Application Data

(60) Provisional application No. 62/383,989, filed on Sep. 6, 2016, provisional application No. 62/383,995, filed on Sep. 6, 2016, provisional application No. 62/383,999, filed on Sep. 6, 2016, provisional application No. 62/383,986, filed on Sep. 6, 2016.

(51) Int. Cl.
| | |
|---|---|
| *A61M 5/142* | (2006.01) |
| *A45F 5/02* | (2006.01) |
| *A61M 5/14* | (2006.01) |
| *A61M 25/02* | (2006.01) |

(52) U.S. Cl.
CPC ........... *A61M 5/14244* (2013.01); *A45F 5/02* (2013.01); *A45F 5/021* (2013.01); *A61M 5/1414* (2013.01); *A61M 5/1415* (2013.01); *A45F 2005/025* (2013.01); *A45F 2200/05* (2013.01); *A61M 2005/1416* (2013.01);
(Continued)

(58) Field of Classification Search
CPC ...... A61M 5/14244; A61M 2025/0206; A61M 2025/024; A61M 25/02; A61M 5/1417; A61M 2005/1416; A61M 2202/04; A61M 2209/082; A61M 2209/088; A61M 5/1414; A61M 5/1415; A45C 2011/002; G06F 1/163; Y10T 24/13; Y10T 24/1391; Y10T 24/1394; A45F 2005/025; A45F 2200/05; A45F 5/02; A45F 5/021
See application file for complete search history.

(56) References Cited

U.S. PATENT DOCUMENTS

| | | |
|---|---|---|
| 4,562,751 A | 1/1986 | Nason et al. |
| 4,678,408 A | 7/1987 | Nason et al. |
| (Continued) | | |

*Primary Examiner* — Brandy S Lee
(74) *Attorney, Agent, or Firm* — Lorenz & Kopf, LLP

(57) ABSTRACT

A pump clip for a fluid infusion device is provided. The pump clip includes a mount. The mount includes wings defined on opposed sides of the mount, a first lock tab to couple the pump clip to the fluid infusion device and a lip. The pump clip includes a base coupled to the mount that defines a second lock tab that engages with the lip to retain the mount in a first position. The mount is pivotable about a first pivot axis into a second position in which the mount is spaced apart from the base. The pump clip includes a clip coupled to the base, the clip pivotable about a second pivot axis relative to the base between a first, clamped position and a second, released position to receive an article.

20 Claims, 24 Drawing Sheets

(52) U.S. Cl.
CPC ... *A61M 2025/024* (2013.01); *A61M 2202/04* (2013.01); *A61M 2209/082* (2013.01); *A61M 2209/088* (2013.01)

(56) References Cited

U.S. PATENT DOCUMENTS

| | | | |
|---|---|---|---|
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2003/0106917 A1 | 6/2003 | Sheller et al. |
| 2003/0110595 A1 | 6/2003 | Collins et al. |
| 2007/0123819 A1 | 5/2007 | Mernoe et al. |
| 2008/0269687 A1 | 10/2008 | Chong et al. |
| 2009/0299290 A1 | 12/2009 | Moberg |
| 2010/0160861 A1 | 6/2010 | Causey, III et al. |
| 2013/0126565 A1* | 5/2013 | Rostami .......... A45F 5/021 224/191 |
| 2016/0256623 A1* | 9/2016 | Crane .......... A61M 5/14244 |

* cited by examiner

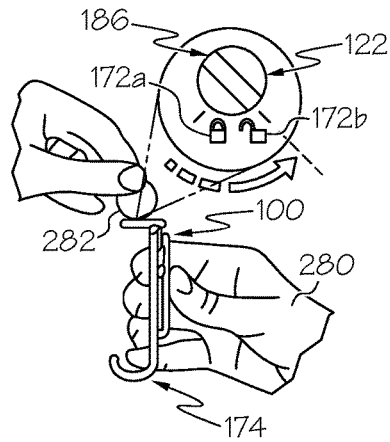
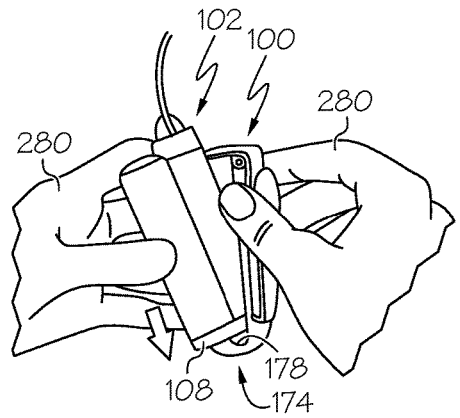
FIG. 9A  FIG. 9B
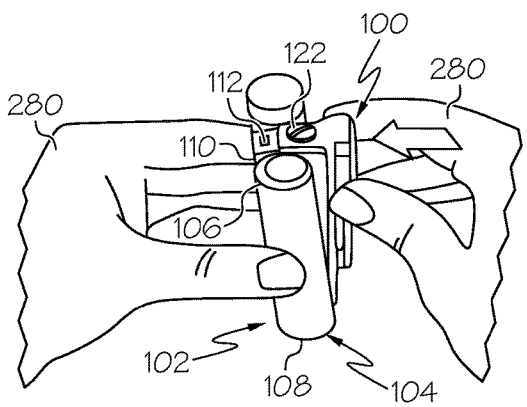
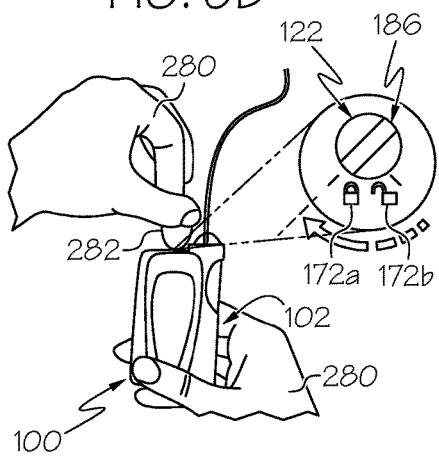
FIG. 9C  FIG. 9D
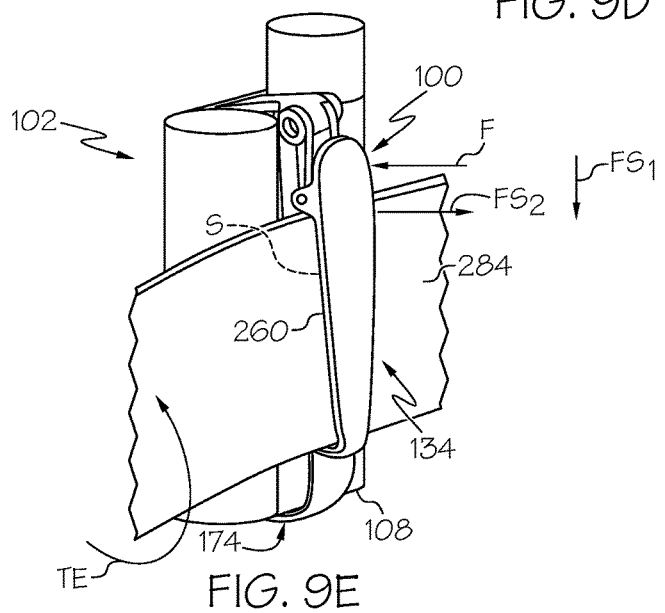
FIG. 9E

PUMP CLIP FOR A FLUID INFUSION DEVICE

CROSS-REFERENCE TO RELATED APPLICATIONS

This application claims the benefit of U.S. Provisional Application No. 62/383,989, filed on Sep. 6, 2016. This application also claims the benefit of U.S. Provisional Application No. 62/383,995, filed on Sep. 6, 2016. This application claims the benefit of U.S. Provisional Application No. 62/383,999, filed on Sep. 6, 2016. This application also claims the benefit of U.S. Provisional Application No. 62/383,986, filed on Sep. 6, 2016. The disclosure of each of the above referenced applications is incorporated herein by reference.

TECHNICAL FIELD

Embodiments of the subject matter described herein relate generally to fluid infusion devices for delivering a medication fluid to the body of a user. More particularly, embodiments of the subject matter relate to a pump clip for a portable fluid infusion device that securely couples the fluid infusion device to the user and withstands accidental displacement of the fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. Generally, external fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the user via, for example, a set connector of an infusion set, which is coupled to the fluid reservoir.

In the example of the external fluid infusion device as an insulin infusion device, the external fluid infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device.

In this instance, as the device is used continuously for delivering insulin twenty-four hours a day, it is desirable to secure the device to the body of the user. In certain instances, a pump clip can enable easy access to the external infusion device while allowing the fluid infusion device to be securely held in position while being discrete and inconspicuous. Given that a pump clip is often secured to a user's clothing, however, the fluid infusion device is susceptible to accidental displacement, caused by bumping/snagging on chairs, seat belts when exiting a vehicle, contact with door knobs/tables, etc. The accidental displacement may pull the pump clip away from the fluid infusion device, which may cause damage to the pump clip and/or the fluid infusion device. In addition, movement of the infusion set from accidental displacement of the fluid infusion device or tubing may adversely affect the delivery and efficacy of the infusion therapy.

Accordingly, it is desirable to provide a pump clip for a fluid infusion device that securely couples the fluid infusion device to the user while reducing a likelihood of damage to the pump clip and/or fluid infusion device from accidental or unintentional displacement of the fluid infusion device. Furthermore, other desirable features and characteristics will become apparent from the subsequent detailed description and the appended claims, taken in conjunction with the accompanying drawings and the foregoing technical field and background.

BRIEF SUMMARY

According to various embodiments, provided is a pump clip for a fluid infusion device. The pump clip includes a mount. The mount includes wings defined on opposed sides of the mount, a first lock tab to couple the pump clip to the fluid infusion device and a lip. The pump clip includes a base coupled to the mount that defines a second lock tab that engages with the lip to retain the mount in a first position. The mount is pivotable about a first pivot axis into a second position in which the mount is spaced apart from the base. The pump clip includes a clip coupled to the base, the clip pivotable about a second pivot axis relative to the base between a first, clamped position and a second, released position to receive an article.

Further provided according to various embodiments is a portable fluid infusion device system. The portable fluid infusion device system includes a fluid infusion device having a pump clip interface that defines a pair of rails. The portable fluid infusion device system includes a pump clip coupled to the pump clip interface. The pump clip includes a mount. The mount includes wings defined on opposed sidewalls of the mount, a first lock tab and a lip. The wings cooperate with the pair of rails to position the pump clip on the fluid infusion device and the first lock tab cooperates with the pump clip interface to releasably couple the pump clip to the fluid infusion device. The pump clip includes a base coupled to the mount that defines a second lock tab that engages with the lip to retain the mount in a first position. The mount is pivotable about a first pivot axis into a second position in which the mount is spaced apart from the base. The pump clip includes a clip coupled to the base and the clip is pivotable about a second pivot axis relative to the base between a first, clamped position and a second, released position to receive an article.

Also provided according to various embodiments is a portable fluid infusion device system. The portable fluid infusion device system includes a fluid infusion device having a pump clip interface that defines a pair of rails and a notch. The portable fluid infusion device system includes a pump clip coupled to the pump clip interface. The pump clip includes a mount. The mount includes wings defined on opposed sidewalls of the mount, a first lock tab and a lip. The wings are configured to be slidably received within the pair of rails to position the pump clip on the fluid infusion device. The first lock tab cooperates with the notch of the pump clip interface to releasably couple the pump clip to the fluid infusion device. The pump clip includes a base coupled to the mount that defines a second lock tab that engages with the lip to retain the mount in a first position. The mount is pivotable about a first pivot axis into a second position in which the mount is spaced apart from the base. The pump clip includes a clip coupled to the base and the clip is pivotable about a second pivot axis relative to the base between a first, clamped position and a second, released position to receive an article.

According to various embodiments, provided is a pump clip for a fluid infusion device. The pump clip includes a clip base having a first end opposite a second end. The clip base defines an aperture through the clip base between the first end and the second end. The clip base is pivotable between a first position and a second position along a first pivot axis. The pump clip includes a clip pivot base coupled to the clip base along the first pivot axis. At least a portion of the clip pivot base is received within the aperture in the first position. The pump clip includes a clip coupled to the clip pivot base along a second pivot axis and the clip cooperates with the clip pivot base to receive an article.

Further provided according to various embodiments is a portable fluid infusion device system. The portable fluid infusion device system includes a fluid infusion device having a first end opposite a second end. The portable fluid infusion device system includes a pump clip coupled to the first end and to the second end. The pump clip includes a clip base having a first base end opposite a second base end. The clip base defines an aperture through the clip base between the first base end and the second base end. The clip base has a first base side opposite a second base side. The second base side is coupled to the fluid infusion device. The clip base is pivotable between a first position and a second position along a first pivot axis. The pump clip includes a clip pivot base coupled to the first base side of the clip base along the first pivot axis such that at least a portion of the clip pivot base is received within the aperture in the first position and the clip pivot base is spaced apart from the clip base in the second position. The pump clip includes a clip coupled to the clip pivot base along a second pivot axis and the clip cooperates with the clip pivot base to define a slot to receive an article.

Also provided according to various embodiments is a portable fluid infusion device system. The portable fluid infusion device system includes a fluid infusion device having a first end opposite a second end. The portable fluid infusion device system includes a pump clip coupled to the first end and to the second end. The pump clip includes a clip base having a first base end opposite a second base end. The clip base defines an aperture through the clip base between the first base end and the second base end. The clip base has a first base side opposite a second base side. The second base side is coupled to the fluid infusion device. The clip base is pivotable between a first position and a second position along a first pivot axis. The pump clip includes a clip pivot base coupled to the first base side of the clip base along the first pivot axis such that at least a portion of the clip pivot base is received within the aperture in the first position and the clip pivot base is spaced apart from the clip base in the second position. The pump clip includes a first biasing member coupled to the clip base that biases the clip base in the first position. The first biasing member includes a first leg coupled to the clip pivot base and a second leg coupled to the clip base. The pump clip includes a clip coupled to the clip pivot base along a second pivot axis and the clip cooperates with the clip pivot base to define a slot to receive an article.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 9A is a schematic environmental illustration of a first action for coupling the pump clip of FIG. 2 to the fluid infusion device of FIG. 1, which illustrates moving a lock button of the pump clip from a lock position to an unlock position;

FIG. 9B is a schematic environmental illustration of a second action for coupling the pump clip of FIG. 2 to the fluid infusion device of FIG. 1, which illustrates positioning a base clip of the pump clip around a second end of the fluid infusion device;

FIG. 9C is a schematic environmental illustration of a third action for coupling the pump clip of FIG. 2 to the fluid infusion device of FIG. 1, which illustrates positioning a base clip of the pump clip around a first end of the fluid infusion device;

FIG. 9D is a schematic environmental illustration of a fourth action for coupling the pump clip of FIG. 2 to the fluid infusion device of FIG. 1, which illustrates moving the lock button of the pump clip from the unlock position to the lock position;

FIG. 9E is a schematic environmental illustration of a fifth action for coupling the pump clip of FIG. 2 to the fluid infusion device of FIG. 1, which illustrates positioning an article associated with a user in the pump clip;

DETAILED DESCRIPTION

Figure 1:
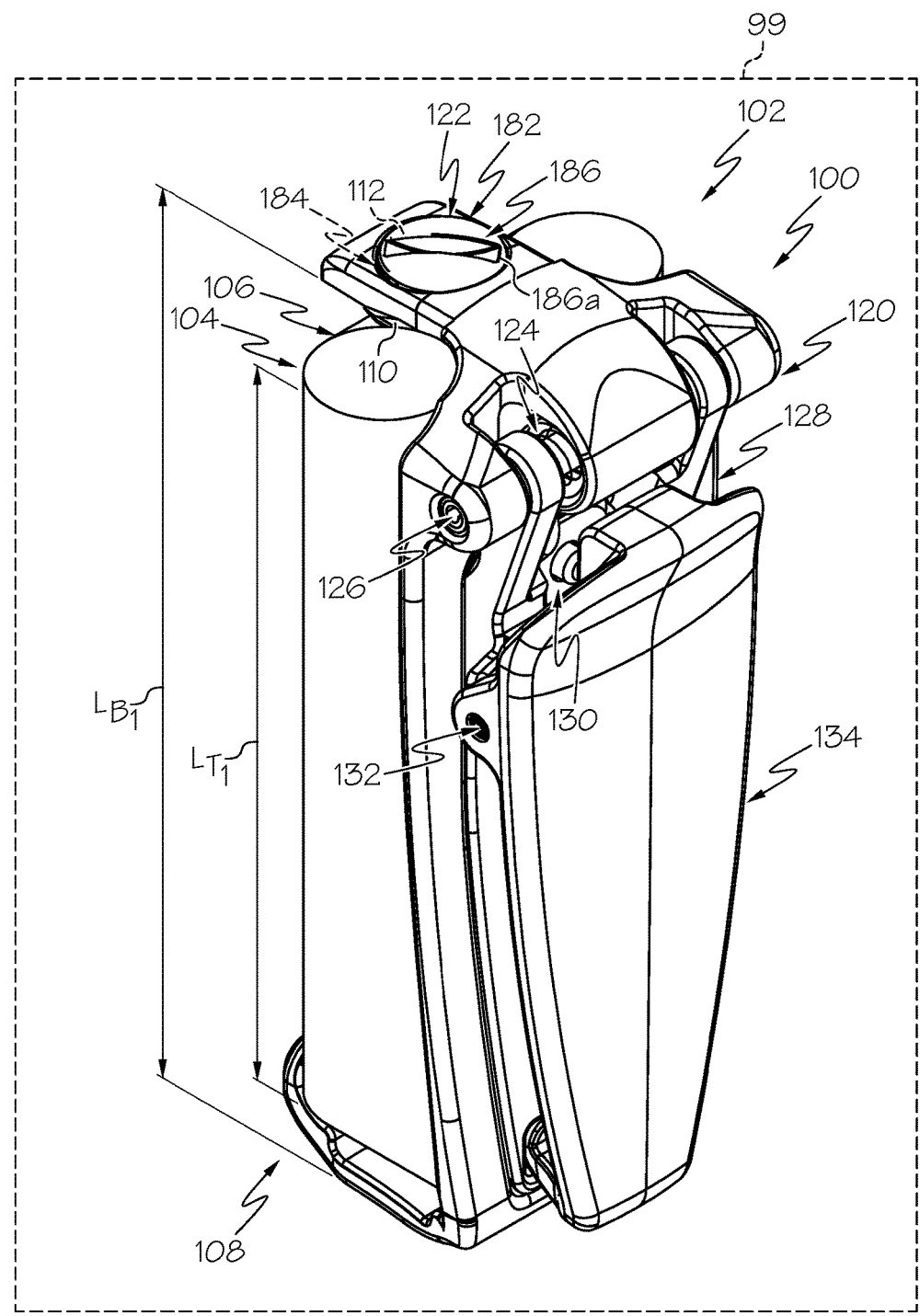
FIG. 1 is a perspective view of an exemplary pump clip for an exemplary fluid infusion device according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description relates to various embodiments of a pump clip. The geometry of the pump clip can be configured to accommodate a variety of different portable devices such as, but not limited to, portable external infusion systems. In one example, the pump clip is provided for use with a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Generally, the pump clip configured to hold an external infusion device, such as a fluid infusion device, has various design challenges that generally are not present regarding many other portable electronic devices. For example, with some embodiments the infusion device is directly connected via tubing to an infusion set having a cannula inserted into the user. Thus, while pump clips for portable electronic devices can allow the electronic device to spin freely, if applied to a portable infusion device the free rotation could lead to tangled or displaced tubing and may displace the infusion set. Moreover, since the pump clip is in contact with the user, the size and geometry of the pump clip needs to be comfortable to wear, and the pump clip needs to be able to attach to a variety of areas on the user or to various articles or objects associated with the user to enable the fluid infusion device to be worn at various locations. Additionally, given the repeated contact with the user, the pump clip needs to be composed of a material resistant to exposure to chemicals, such as sun screen, body lotion, finger oils, and detergents to prolong a useful life of the pump clip.

Figure 1A:
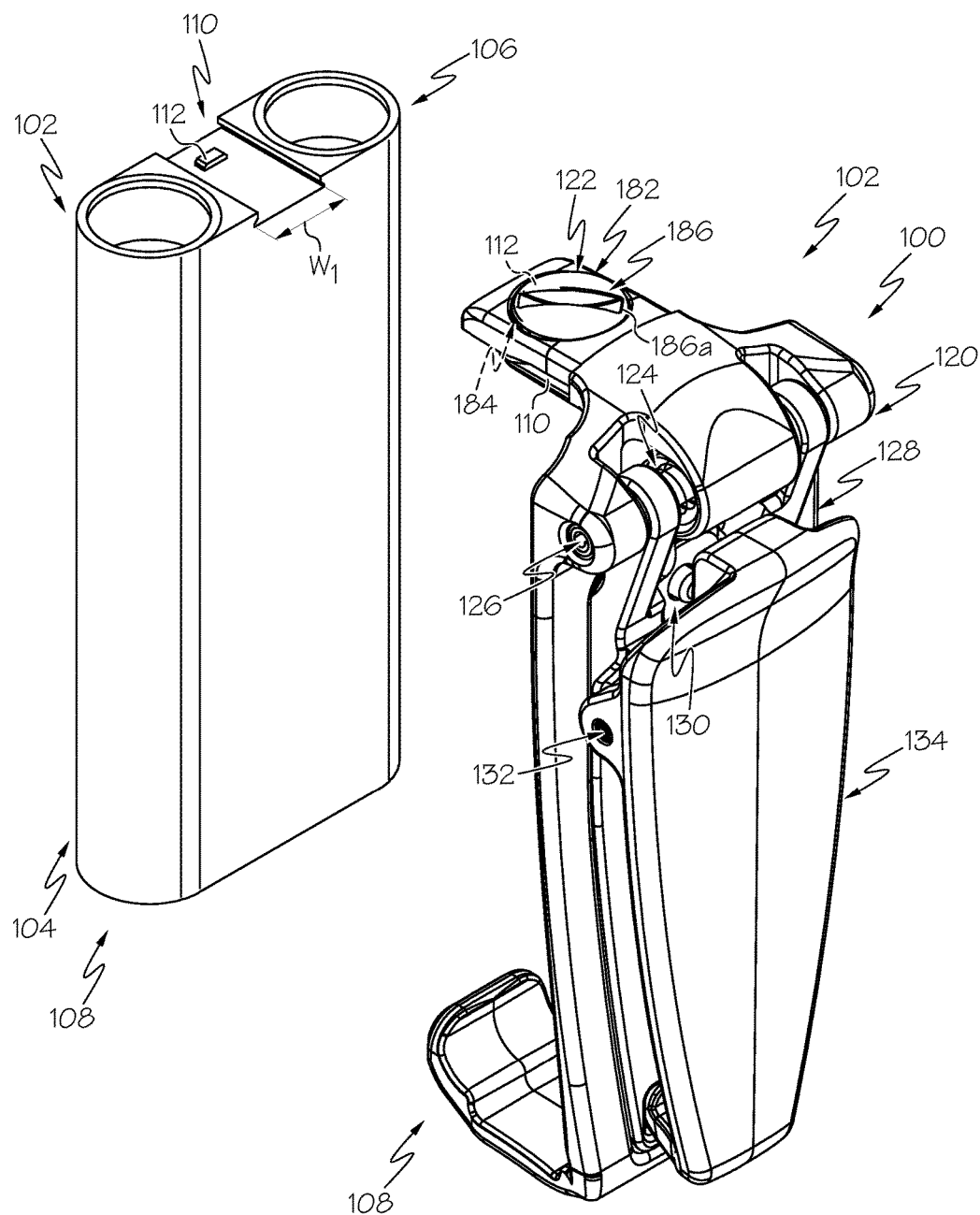
FIG. 1A is a perspective view of the pump clip of FIG. 1 exploded from the fluid infusion device of FIG. 1.

With reference to FIG. 1, a pump clip 100 is shown coupled to a fluid infusion device 102. In FIG. 1A, the pump clip 100 is shown removed from the fluid infusion device 102. The pump clip 100 and the fluid infusion device 102 cooperate to define a portable fluid infusion device system 99 (FIG. 1). The fluid infusion device 102 may be any fluid infusion device known in the art, and thus, the fluid infusion device 102 will not be discussed in great detail herein. Generally, the fluid infusion device 102 is designed to be carried or worn by the user, and to be coupled to the user via the pump clip 100. In one example, the fluid infusion device 102 is an insulin infusion device, such as the MiniMed Paradigm® 500 series Insulin Pump, which is commercially available from Medtronic MiniMed, Inc. of Northridge, Calif. The fluid infusion device 102 may leverage a number of conventional features, components, elements, and characteristics described in U.S. Pat. Nos. 6,485,465 and 7,621, 893, the relevant content of which is incorporated by reference herein.

Briefly, with reference to FIGS. 1 and 1A, the fluid infusion device 102 includes a housing 104. The housing 104 has a first end 106 and an opposite second end 108. The first end 106 defines a slot 110 and a protrusion 112 (FIG. 1A). The slot 110 receives a portion of the pump clip 100 to assist in securing the pump clip 100 to the first end 106 of the fluid infusion device 102. The slot 110 has a width W1 (FIG. 1A), which is sized to receive the portion of the pump clip 100. The slot 110 may have inward sloping sides to facilitate the alignment of the pump clip 100 with the slot 110. With brief reference to FIG. 1A, the protrusion 112 extends outwardly from the slot 110. The protrusion 112 cooperates with a portion of the pump clip 100 to retain the pump clip 100 on the housing 104 and coupled to the fluid infusion device 102. The protrusion 112 generally comprises a rounded tab; however, the protrusion 112 may have any desired shape to cooperate with the pump clip 100. With reference back to FIG. 1, as will be discussed, the second end 108 is received within a portion of the pump clip 100.

Figure 2:
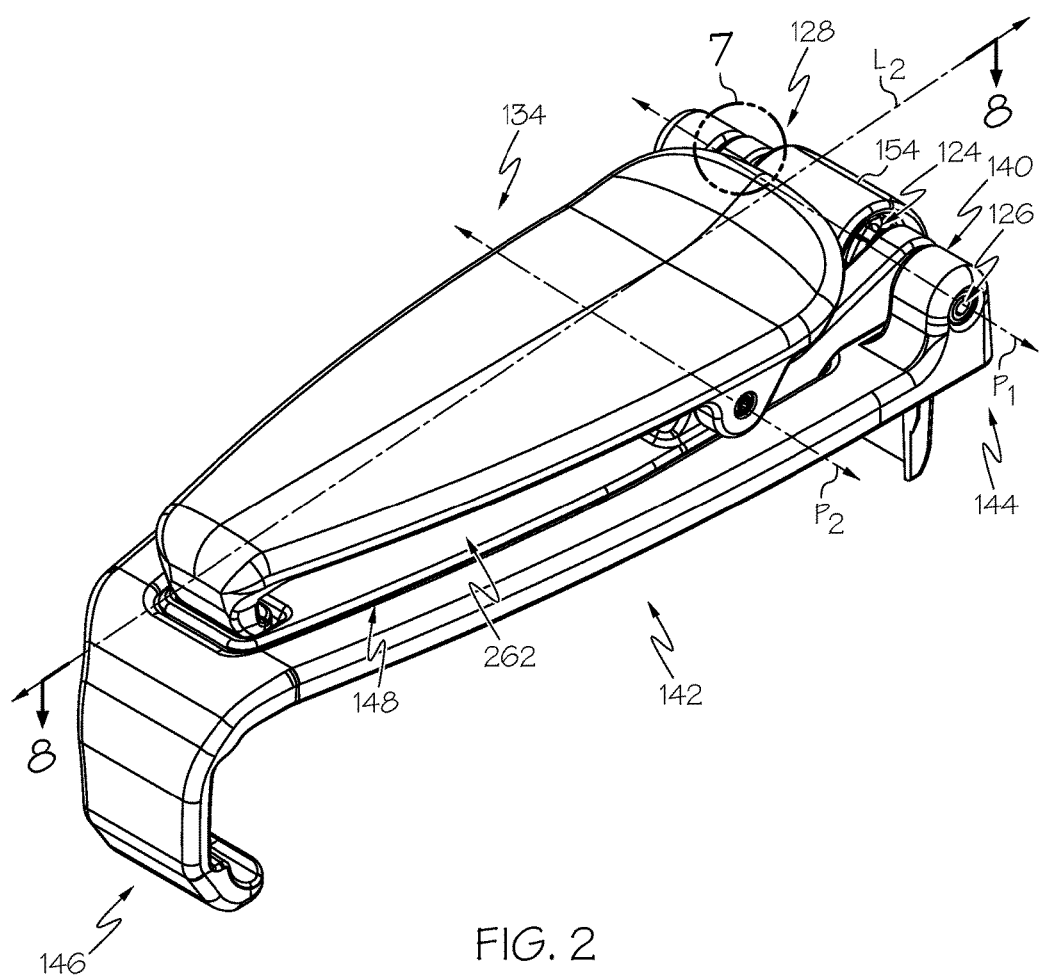
FIG. 2 is perspective view of the pump clip of FIG. 1 removed from the fluid infusion device, in which a clip base is shown in a first position and a clip of the pump clip is shown in a first, clamp position.

The pump clip 100 includes a clip base 120, a lock button 122, a first biasing member or first spring 124, a hinge pin 126, a clip pivot base 128, a second biasing member or second spring 130, a clamp pin 132 and a clip 134. With reference to FIG. 2, the pump clip 100 is shown detached from the fluid infusion device 102. As shown, the clip base 120 is configured to receive the fluid infusion device 102. The clip base 120 includes a first base side 140 opposite a second base side 142, a first base end 144 opposite a second base end 146 and an aperture 148. The clip base 120 is generally composed of a biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. In one example, the clip base 120 is composed of Tritan® COPOLYESTER MX711. The clip base 120 may be formed using casting, printing, molding or another suitable technique.

Figure 3:
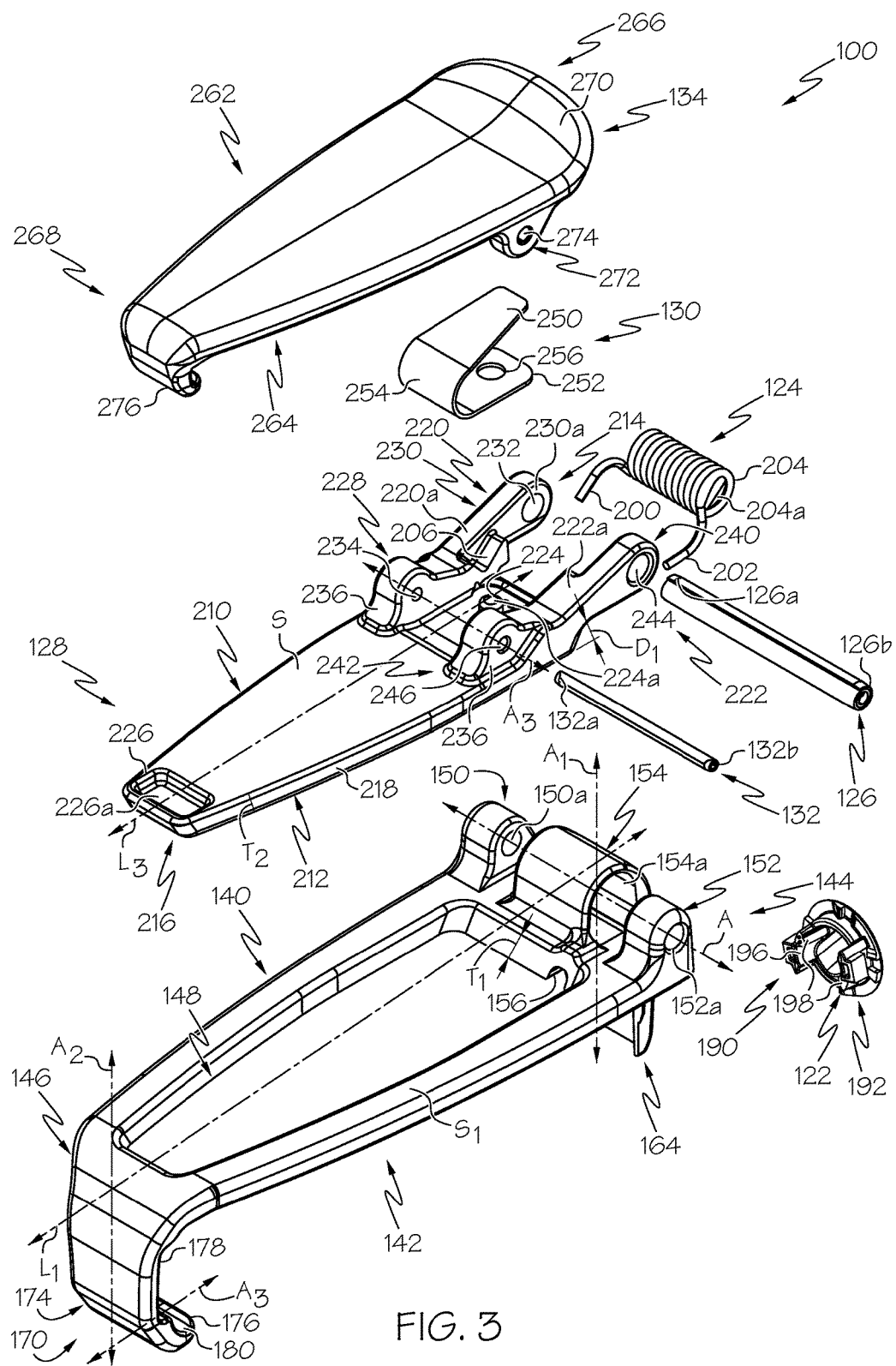
FIG. 3 is an exploded view of the pump clip of FIG. 2.

With reference to FIG. 3, the first base side 140 includes or defines a first pin post 150, a second pin post 152 and a spring cover 154. The first pin post 150 and the second pin post 152 extend outwardly from the first base side 140. The first pin post 150 and the second pin post 152 are rounded to provide a smooth contact surface against the user. The first pin post 150 defines a first bore 150a, and the second pin post defines a second bore 152a. The first bore 150a receives a first end 126a of the hinge pin 126, and the second bore 152a receives an opposite second end 126b of the hinge pin 126. The first pin post 150 and the second pin post 152 cooperate to retain the hinge pin 126 on the clip base 120. The first bore 150a and the second bore 152a are defined in the respective first pin post 150 and the second pin post 152 along an axis A, which is substantially perpendicular to the longitudinal axis L1 of the clip base 120.

The spring cover 154 is arcuate, and may be substantially cylindrical. The spring cover 154 is defined on the first base side 140 so as to be substantially evenly spaced apart from the first pin post 150 and the second pin post 152. Stated another way, the spring cover 154 is substantially centered on the first base body 140 between the first pin post 150 and the second pin post 152. The spring cover 154 is spaced apart from the first pin post 150 and the second pin post 152 such that respective portions of the clip pivot base 128 may be received between the first pin post 150 and the spring cover 154, and between the second pin post 152 and the spring cover 154. The spring cover 154 protects the first spring 124, and substantially encloses a portion of a body of the first spring 124 such that the first spring 124 is substantially concealed from view when the pump clip 100 is assembled (FIG. 2). The spring cover 154 defines a spring aperture 154a, which cooperates with the second base side 142 to receive the first spring 124.

Figure 4:
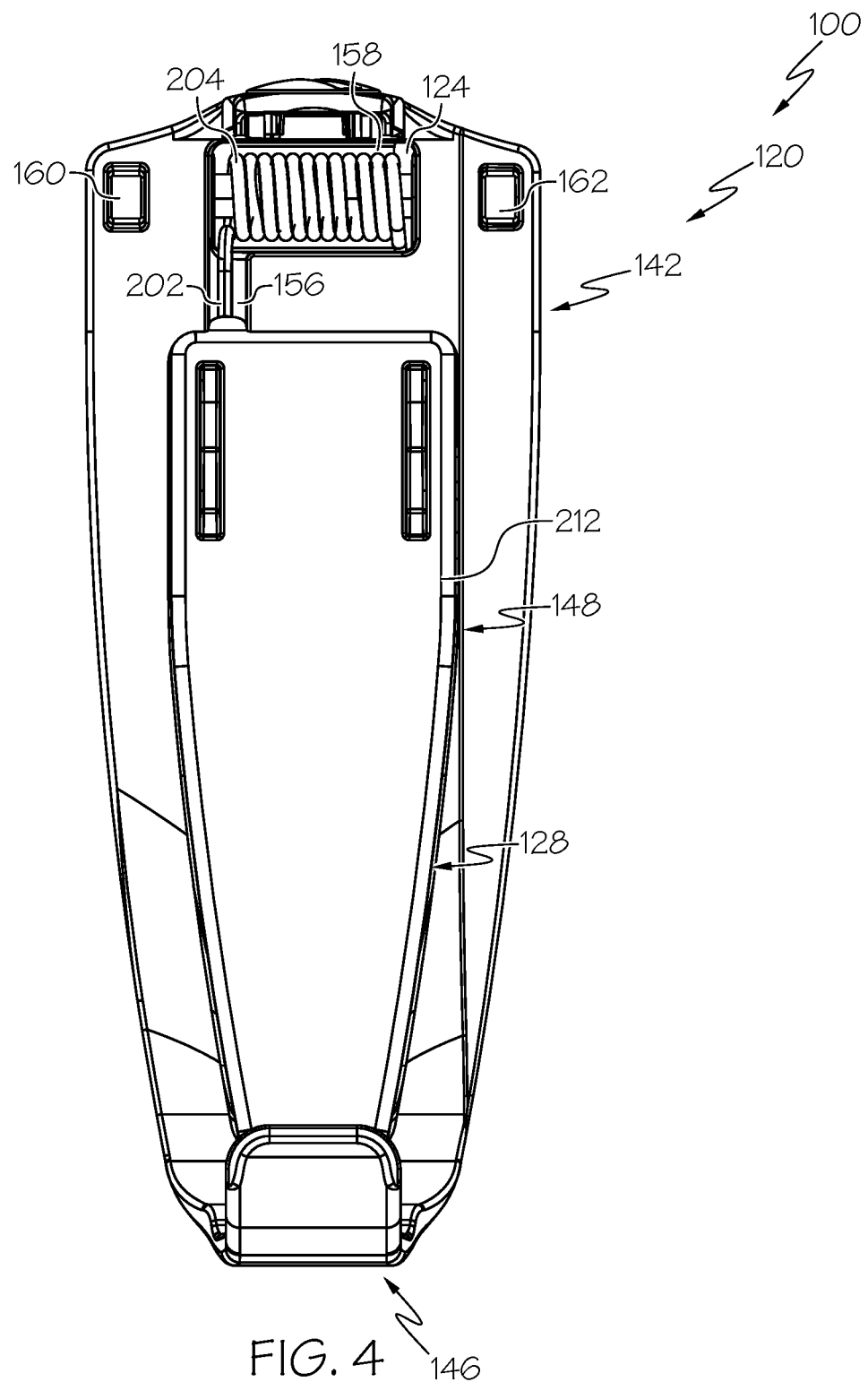
FIG. 4 is rear view of the pump clip of FIG. 2.

With reference to FIG. 4, the second base side 142 is shown in greater detail. The second base side 142 is substantially flat or planar for being positioned against the fluid infusion device 102 (FIG. 1) when the fluid infusion device 102 is coupled to the pump clip 100. The second base side 142 includes a spring guide 156, a spring recess 158, a first pocket or relief 160 and a second pocket or relief 162. The spring guide 156 is defined as a concave notch on the second base side 142, which extends between the spring recess 158 and the aperture 148. The spring guide 156 receives a portion of the first spring 124. The spring recess 158 is in communication with the spring cover 154 and cooperates with the spring cover 154 to receive the first spring 124. The first relief 160 is defined on the second base surface 142 so as to be substantially opposite the second pin post 152 (FIG. 3). The second relief 162 is defined on the second base surface 142 so as to be substantially opposite the first pin post 150 (FIG. 3). The first relief 160 and the second relief 162 may provide a mass savings and may aid in the manufacture of the clip base 120.

Figure 5:
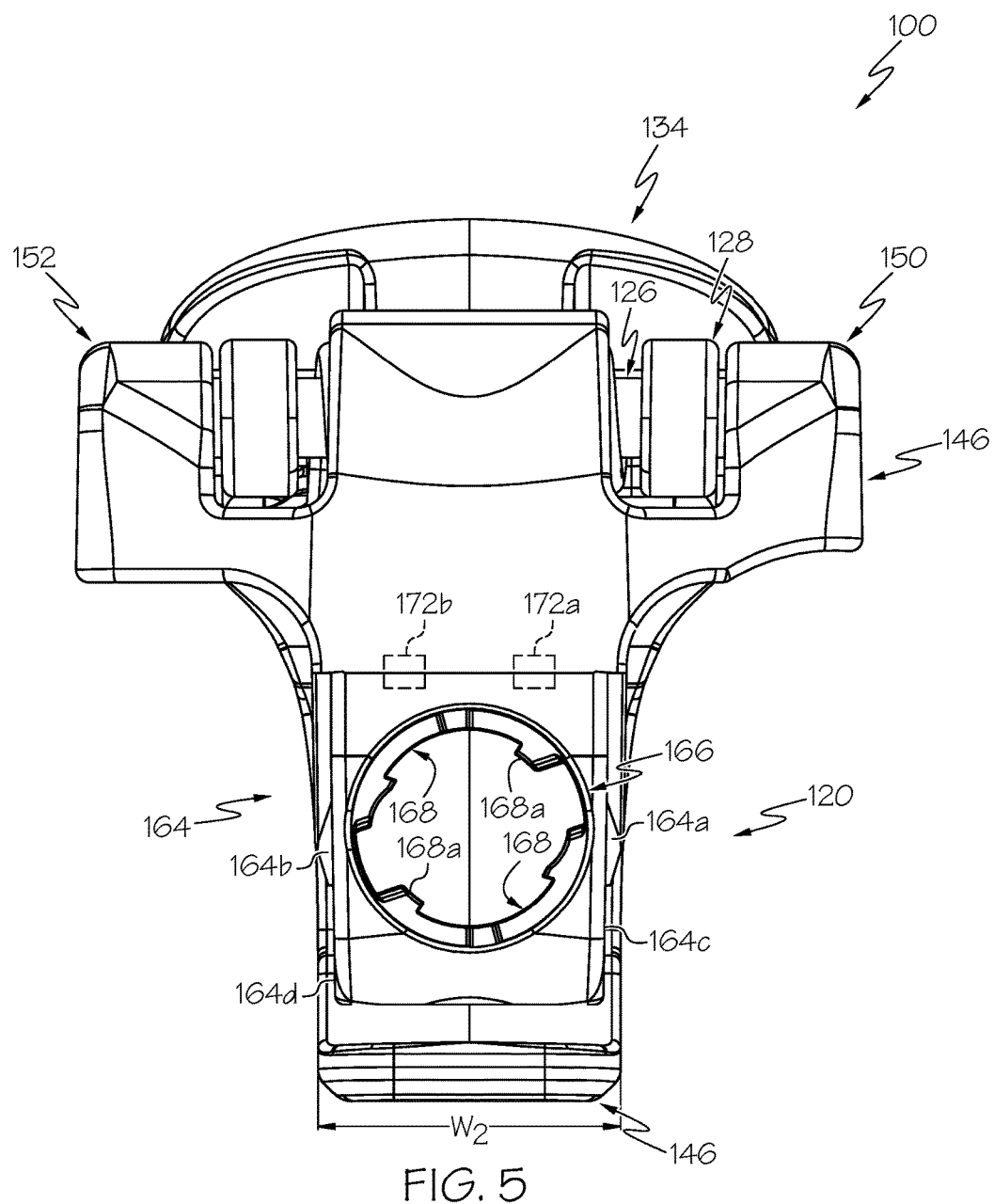
FIG. 5 is an end view of the pump clip of FIG. 2.

With reference to FIG. 5, the first base end 144 includes a coupling flange 164. The coupling flange 164 extends outwardly form the first base end 144, and generally extends along an axis A1, which is substantially perpendicular to the longitudinal axis L1 of the clip base 120 (FIG. 3). The coupling flange 164 has a width W2, which is substantially equal to the width W1 of the slot 110 (FIG. 1) so that the coupling flange 164 may be received onto the fluid infusion device 102. The coupling flange 164 may also include one or more protrusions, such as a first protrusion 164a and a second protrusion 164b. The first protrusion 164a and the second protrusion 164b extend outwardly from a respective side 164c, 164d of the coupling bore 166 and cooperate with mating features defined in the slot 110 to assist in coupling the pump clip 100 to the fluid infusion device 102. In one example, the first protrusion 164a and the second protrusion 164b cooperate to form a dovetail with the slot 110 (FIG. 1A).

The coupling flange 164 also defines a coupling bore 166, which receives the lock button 122. The coupling bore 166 includes a plurality of ridges 168, which are spaced apart about a circumference of the coupling bore 166. Each of the plurality of ridges 168 cooperate with a respective one of a plurality of reliefs 170 defined on the lock button 122 (FIG. 3) to retain the lock button 122 within the coupling bore 166. In this example, each of the plurality of ridges 168 include a bulbous portion 168a, which assists in retaining the lock button 122 within the coupling bore 166. Each of the plurality of ridges 168 are defined about a perimeter of the coupling bore 166 and extend radially inward toward a center of the coupling bore 166. The coupling flange 164 may also include one or more graphical indicators 172, such as a lock symbol 172a and an unlock symbol 172b, as shown in FIGS. 12A and 12D, if desired. The lock symbol 172a and the unlock symbol 172b provide a visual indicator of a lock position and an unlock position, respectively, for the pump clip 100 relative to the fluid infusion device 102, as will be discussed further herein.

With reference to FIG. 3, the second base end 146 is substantially C-shaped to fit around the second end 108 of the fluid infusion device 102 (FIG. 1). The second base end 146 includes a coupling portion 174 and a lip 176. The coupling portion 174 extends outwardly away from the clip base 120 along an axis A2. The axis A2 is substantially parallel to the axis A1, and is substantially perpendicular to the longitudinal axis L1. The coupling portion 174 defines a channel 178. The channel 178 is sized to be adjacent to the second end 108 of the fluid infusion device 102 (FIG. 1) to couple the fluid infusion device 102 to the pump clip 100. Generally, the channel 178 enables the pump clip 100 to clear a bumper defined on a bottom of the housing 104 of the fluid infusion device 102. The lip 176 extends outwardly away from the coupling portion 174 along an axis A3. The axis A3 is substantially perpendicular to the axis A2, and substantially parallel to the longitudinal axis L1 of the clip base 120. A curved surface 180 is defined between the lip 176 and the coupling portion 174 to assist in coupling the fluid infusion device 102 to the pump clip 100. The lip 176 and the curved surface 180 cooperate to guide the fluid infusion device 102 into the coupling portion 174.

The aperture 148 is defined through the first base side 140 and the second base side 142 and extends from the near the first base end 144 to the second base end 146. The aperture 148 has a thickness T1, which is sized and shaped to correspond to a portion of the clip pivot base 128. The aperture 148 is in communication with the spring guide 156.

As will be discussed, the lock button 122 is received within the coupling bore 166 and retains the pump clip 100 on the fluid infusion device 102. The lock button 122 may be optional, in that the pump clip 100 may be snap-fit around the fluid infusion device 102, if desired. In this example, with reference to FIG. 1, the lock button 122 includes a first end 182 and an opposite second end 184. The lock button 122 is generally cylindrical in shape, and is composed of a biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. In one example, the lock button 122 is composed of Tritan® COPOLYESTER MX711. The lock button 122 may be formed using casting, printing, molding or another suitable technique. The first end 182 includes a key slot 186. The key slot 186 has a concave bottom surface 186a that is shaped to receive an implement for moving or rotating the lock button 122 between a lock position and an unlock position. In one example, the instrument is a coin; however, the instrument may include a screwdriver, fingernail, or other device capable of being received in the key slot 186 and applying a force to move or rotate the lock button 122 within the coupling bore 166.

Figure 6:
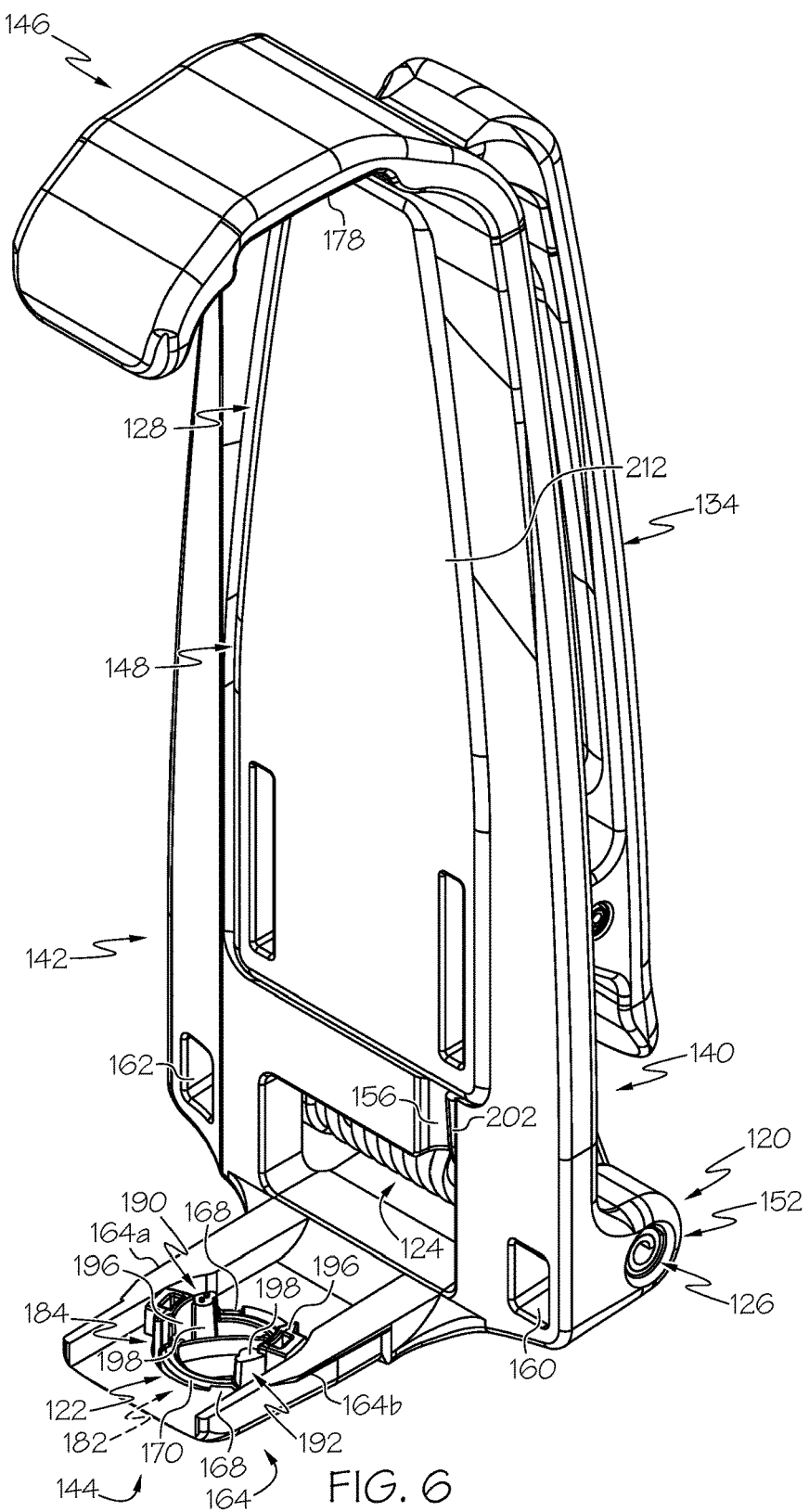
FIG. 6 is a rear perspective view of the pump clip of FIG. 2.

With reference to FIG. 6, the second end 184 of the lock button 122 includes a first lock 190 spaced apart from a second lock 192 and the plurality of reliefs 170. The plurality of reliefs 170 are defined about a perimeter or circumference of the lock button 122 near the first end 182, and cooperate with the plurality of ridges 168 to retain the lock button 122 on the coupling flange 164.

The first lock 190 is spaced apart from the second lock 192 about the perimeter or circumference of the lock button 122. In one example, the first lock 190 is substantially opposite the second lock 192 about the circumference of the lock button 122. The first lock 190 and the second lock 192 include a lock guide 196 and a lock protrusion 198. The lock guide 196 guides the lock button 122 about the protrusion 112 of the fluid infusion device 102 (FIG. 1) to position the lock protrusion 198 into contact with the protrusion 112 (FIG. 1). The contact between the lock protrusion 198 and the protrusion 112 retains the pump clip 100 on the fluid infusion device 102 and inhibits the pump clip 100 from sliding off of the fluid infusion device 102. The lock guides 196 are received through the coupling bore 166, and once the lock button 122 is rotated past the one of the plurality of ridges 168, the lock guides 196 retain the lock button 122 within the coupling bore 166. Stated another way, the lock guides 196 sit under the plurality of ridges 168, while the lock protrusions 198 slide over a top surface of the plurality of ridges 168.

The first spring 124 is received within the clip base 120 and enables the clip base 120 to rotate relative to or away from the clip pivot base 128 upon the application of a torque greater than the first spring torque of the first spring 124. Thus, the first spring 124 enables the clip base 120 to move from a first position (FIG. 2) to a second position and positions in-between (FIG. 10) upon the application of a torque to the fluid infusion device 102 greater than the first spring torque of the first spring 124. As shown, in the first position the clip base 210 is adjacent to or next to the clip pivot base 128, and in the second position, the clip base 210 is spaced apart from the clip pivot base 128. In one example, the first spring torque applied by the first spring 124 is about 4.3 inch-ounces (in.-oz.) at the first position (fully closed position), and is about 17.5 inch-ounces (in.-oz.) at the second position (fully open position).

The first spring 124 biases the clip base 120 in the first position, and upon removal of a torque that has moved the clip base 120 towards the second position, the first spring 124 returns the clip base 120 to the first position. Thus, the first spring 124 enables the pump clip 100 to withstand torques caused by the fluid infusion device 102 contacting external factors without damaging the fluid infusion device 102 and/or the pump clip 100, and without impacting an infusion set coupled percutaneously to the user. The first spring 124 also enables the user to apply a torque to rotate the fluid infusion device 102 without damaging the fluid infusion device 102 and/or the pump clip 100, and without impacting an infusion set coupled percutaneously to the user. In one example, the first spring 124 withstands a torque acting on the fluid infusion device 102 that is less than about 4.3 inch-ounces (in.-oz.). Thus, a torque applied to the fluid infusion device 102 that is greater than about 4.3 inch-ounces (in.-oz.) causes the clip base 120 to move or rotate toward the second position. The first spring 124 is composed of a biocompatible metal or metal alloy, such as a nickel coated music wire. The first spring 124 may be formed through any suitable technique, such as extrusion, casting, etc. In this example, the first spring 124 is a helical torsion spring, and includes a first spring leg 200 and a second spring leg 202, which extend from opposite sides of a helical coil body 204. Thus, the first spring leg 200 is at a first end of the helical coil body 204, and the second spring leg 202 is at a second end of the helical coil body 204.

Figure 7:
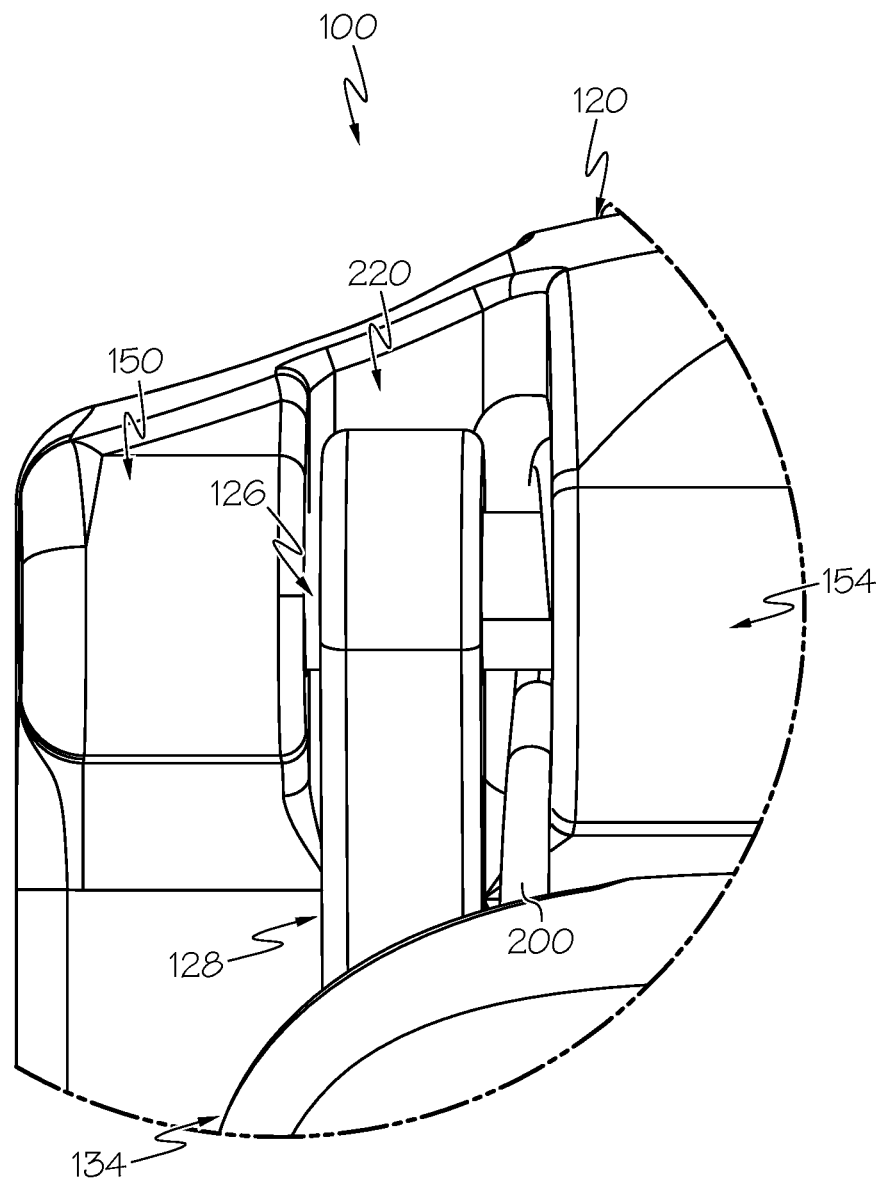
FIG. 7 is a detail view of the pump clip of FIG. 2, taken at 7 on FIG. 2, which illustrates a first leg of a first biasing member received within a clip pivot base of the pump clip.

The first spring leg 200 is coupled to the clip pivot base 128. In one example, the first spring leg 200 may be received within a pivot spring guide 206 defined on a portion of the clip pivot base 128. With reference to FIG. 7, a portion of the first spring leg 200 may be substantially covered by the clip 134 when the pump clip 100 is assembled to assist in retaining the first spring leg 200 within the pivot spring guide 206.

With reference to FIG. 4, the second spring leg 202 is coupled to the clip base 120. In this example, the second spring leg 202 is coupled to the spring guide 156 of the second base side 142 of the clip base 120. The helical coil body 204 is received within the spring recess 158. With reference to FIG. 2, the spring cover 154 substantially encloses the helical coil body 204 to protect the helical coil body 204 and to protect the user from the helical coil body 204. The helical coil body 204 defines an internal passage 204a that receives the hinge pin 126 therethrough.

With reference to FIG. 2, the hinge pin 126 defines a first pivot axis P1 for the movement or rotation of the clip base 120 relative to the clip pivot base 128. The first pivot axis P1 is a first pivot axis for the pump clip 100, and the first pivot axis P1 is substantially perpendicular to a longitudinal axis L2 of the pump clip 100. With reference back to FIG. 3, the hinge pin 126 has the first end 126a that is received within the first pin post 150, and the opposite second end 126b that is received within the second pin post 152. The hinge pin 126 is composed of a biocompatible material, and in one example, is composed of a biocompatible metal or metal alloy. In this example, the hinge pin 126 is composed of a biocompatible sheet of metal or metal alloy, such as a stainless steel, which is rolled into a spiral cylinder. By providing the hinge pin 126 as cylindrical rolled sheet metal, the hinge pin 126 is easily inserted into the first pin post 150, through a portion of the clip pivot base 128, the first spring 124 and into the second pin post 152, and once inserted, the hinge pin 126 expands to provide a radial force that retains the hinge pin 126 within the first pin post 150 and the second pin post 152.

The clip pivot base 128 is coupled to the clip base 120 and to the clip 134. The clip pivot base 128 is composed of a biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. In one example, the clip pivot base 128 is composed of Tritan® COPOLYESTER MX711. The clip pivot base 128 may be formed using casting, printing, molding or another suitable technique. The clip pivot base 128 includes a first clip side 210 opposite a second clip side 212 and a first clip end 214 opposite a second clip end 216. A wall 218 interconnects the first clip side 210 and the second clip side 212. Generally, the wall 218 is received wholly within the aperture 148 when the clip base 120 is in the first position, such that a primary surface S of the first clip side 210 is substantially flush with a primary surface S1 of the first base side 140. The wall 218 has a thickness T2, which is substantially equal to the thickness T1 of the aperture 148. The primary surface S of the first clip side 210 is substantially flat or planar and smooth, to receive a portion of an article associated with a user of the pump clip, such as a belt, shirt, pants, etc.

The first clip side 210 includes a first pivot arm 220, a second pivot arm 222, a spring retainer 224 and a clip recess 226. The first pivot arm 220 and the second pivot arm 222 are spaced apart on the first clip side 210 near and at the first clip end 214. The first pivot arm 220 includes a first clip post 228, the pivot spring guide 206 and an arm 230 that defines a first pivot bore 232. The first clip post 228 defines a first clip bore 234, which receives a first end 132a of the clamp pin 132. The first clip post 228 also defines a flange relief 236, which enables a portion of the clip 134 to be received over the first clip post 228. In one example, the flange relief 236 is a portion of the first clip post 228 adjacent to the wall 218 that is removed for receipt of the portion of the clip 134. The first pivot arm 220 defines a sloped surface 220a that transitions from the first clip post 228 to the arm 230. The sloped surface 220a provides clearance for a movement or rotation of the clip 134 and acts as a guide for the rotation of the clip 134.

The pivot spring guide 206 is defined between the first clip post 228 and the first pivot bore 232 along a side 230a of the arm 230. The pivot spring guide 206 may extend along an axis that is transverse or oblique to a longitudinal axis L3 of the clip pivot base 128 to aid in retaining the first spring leg 200. The arm 230 extends a distance D1 above the wall 218 so that the arm 230 may rest upon a portion of the first base side 140 to enable the first pivot bore 232 to be coupled to the hinge pin 126. As the distance D1 for the arm 230 of the first pivot arm 220 is the same as the distance D1 for an arm 240 of the second pivot arm 222, the distance D1 is shown in FIG. 3 associated with the arm 240 with the understanding that the distance D1 for the arm 230 is the same. The arm 230 has a width that is sized to be received on the first base side 140 between the first pin post 150 and an end of the spring cover 154. The first pivot bore 232 is defined at a distalmost or terminal end of the arm 230. The first pivot bore 232 receives a portion of the hinge pin 126 therethrough to pivotally couple the clip pivot base 128 to the clip base 120 (FIG. 7).

The second pivot arm 222 includes a second clip post 242 and the arm 240 that defines a second pivot bore 244. The second clip post 242 defines a second clip bore 246, which receives a second end 132b of the clamp pin 132. The first clip bore 234 of the first clip post 228 and the second clip bore 246 extend along an axis A3, which is substantially perpendicular to the longitudinal axis L2 of the clip pivot base 128. The second clip post 242 also defines the flange relief 236, which enables a portion of the clip 134 to be received over the second clip post 242. In this example, the flange relief 236 is a portion of the second clip post 242 adjacent to the wall 218 that is removed for receipt of the portion of the clip 134. The second pivot arm 222 defines a second sloped surface 222a that transitions from the second clip post 242 to the arm 240. The second sloped surface 222a provides clearance for a movement or rotation of the clip 134 and acts as a guide for the rotation of the clip 134.

The arm 240 extends the distance D1 above the wall 218 so that the arm 240 may rest upon a portion of the first base side 140 to enable the second pivot bore 244 to be coupled to the hinge pin 126. The arm 240 has a width that is sized to be received on the first base side 140 between an end of the spring cover 154 and the second pin post 152. The second pivot bore 244 is defined at a distalmost or terminal end of the arm 240. The second pivot bore 244 receives a portion of the hinge pin 126 therethrough to pivotally couple the clip base 120 to the clip pivot base 128 (FIG. 7). The arms 230, 240 may also include a relief on an internal surface that is sized to enable the arms 230, 240 to be positioned on either side of the spring cover 154.

The spring retainer 224 extends outwardly or upwardly from the first clip side 210. In one example, the spring retainer 224 is a post, which is cylindrical. The spring retainer 224 is coupled to the second spring 130 and a head 224a of the spring retainer 224 may act as a stop to limit a compression of the second spring 130.

The clip recess 226 is defined at or near the second clip end 216 and receives a portion of the clip 134. The clip recess 226 cooperates with the clip 134 to define a tortuous path for clamping the pump clip 100 to an article of clothing, for example. In this example, the clip recess 226 is substantially rectangular; however, the clip recess 226 may have any desired shape. In this example, the clip recess 226 has an enclosed bottom surface 226a, however, it should be understood that the clip recess 226 may comprise an aperture, which receives a portion of the clip 134.

With reference to FIG. 4, the second clip side 212 is flush with the second base side 142 when the clip pivot base 128 is in the first position. The second clip side 212 is substantially flat or planar, and may include one or more recesses, which may aid in the manufacture of the clip pivot base 128 and may provide mass savings. With reference back to FIG. 3, the first clip end 214 includes the arms 230, 240, which pivotally couple the clip base 120 to the clip pivot base 128. The second clip end 216 includes the clip recess 226.

The second spring 130 is coupled to the clip pivot base 128. In one example, the second spring 130 is a leaf spring and includes a first leaf 250 and a second leaf 252 interconnected by a substantially U-shaped body 254. The second spring 130 is composed of a biocompatible metal or metal alloy, such as a stainless steel. The second spring 130 may be extruded, cast, stamped, machined or otherwise formed. The first leaf 250 is compressible by a force applied to the clip 134 to move the clip 134 from a first, clamped position to a second, release position. In one example, the force needed to overcome the second spring 130 to move the clip 134 from the first, clamped position (fully closed position) is about 1 pound-force (lbf.), and the force needed to move the clip 134 to the second, release position (fully opened position) is about 6 pound-force (lbf.). The second leaf 252 defines a spring bore 256. The spring bore 256 receives the spring retainer 224 therethrough to couple the second spring 130 to the clip pivot base 128. Generally, the spring bore 256 is circular; however, the spring bore 256 may have any shape that corresponds with the spring retainer 224 to retain the second spring 130 on the clip pivot base 128. The body 254 couples the first leaf 250 to the second leaf 252, and provides a second spring force that maintains the clip 134 in the first, clamped position.

With reference to FIG. 2, the clamp pin 132 defines a second pivot axis P2 for the movement or rotation of the clip 134 relative to the clip pivot base 128 between the first, clamped position, the second, release position and various positions in-between. The second pivot axis P2 is a second pivot axis for the pump clip 100, and the second pivot axis P2 is substantially perpendicular to the longitudinal axis L2 of the pump clip 100 and substantially parallel to the first pivot axis P1. The second pivot axis P2 is offset from or spaced apart from the first pivot axis P1 along the longitudinal axis L2 of the pump clip 100. With reference back to FIG. 3, the clamp pin 132 has the first end 132a that is received within the first clip bore 234 of the first clip post 228, and the opposite second end 132b that is received within the second clip bore 246 of the second clip post 242. The clamp pin 132 is composed of a biocompatible material, and in one example, is composed of a biocompatible metal or metal alloy. In this example, the clamp pin 132 is composed of a biocompatible sheet of metal or metal alloy, such as a stainless steel, which is rolled into a spiral cylinder. By providing the clamp pin 132 as cylindrical rolled sheet metal, the clamp pin 132 is easily inserted into the first clip post 228, through a portion of the clip 134, through the second spring 130 and into the second clip post 242, and once inserted, the clamp pin 132 expands to provide a radial force that retains the clamp pin 132 within the first clip post 228 and the second clip post 242.

The clip 134 cooperates with the primary surface S of the clip pivot base 128 to define a slot, generally indicated by reference numeral 260 in FIG. 2, for receipt of an article of clothing or item associated with the user, such as a shirt, belt, strap, etc. when the clip 134 is in the first, clamped position. The clip 134 is composed of a biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. In one example, the clip 134 is composed of Tritan® COPOLYESTER MX711. The clip 134 may be formed using casting, printing, molding or another suitable technique. The clip 134 includes a first side 262 opposite a second side 264, and a first end 266 opposite a second end 268.

The first side 262 is substantially smooth, and includes an arcuate or curved surface 270 near and at the first end 266. The curved surface 270 provides a location for a thumb of a user, for example, to apply a force to move the clip 134 to the second, release position. The second side 264 is substantially smooth, and includes a pair of clip hinge projections 272, which extend outwardly from the second side 264 near the first end 266. The clip hinge projections 272 are spaced apart from each other on the second side 264. In this example, each of the clip hinge projections 272 includes a clip bore 274, which receives a respective first end 132a and second end 132b of the clamp pin 132.

Figure 8:
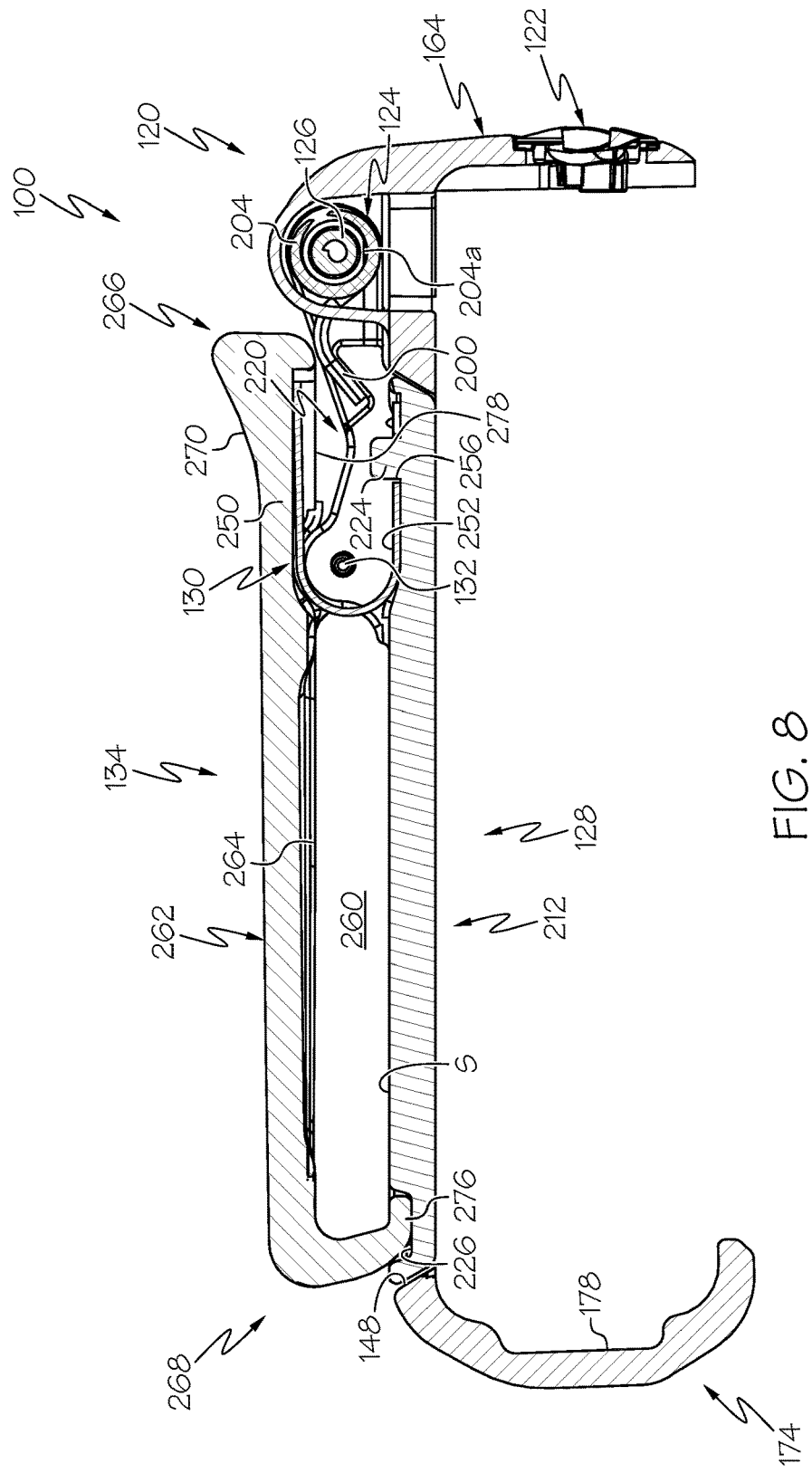
FIG. 8 is a cross-sectional view of the pump clip of FIG. 2, taken along line 8-8 of FIG. 2.

The second side 264 also includes a clip projection 276 at the second end 268. The clip projection 276 extends outwardly from the second side 264, and is substantially U-shaped. With reference to FIG. 8, the clip projection 276 cooperates with the clip recess 226 to define a tortuous path for capturing an article of clothing or other item associated with the user to secure the pump clip 100 to the particular article of clothing or other item. Thus, the clip projection 276 enables the clip 134 to clamp onto an article of clothing or other item associated with the user, and the slot 262 also enables the pump clip 100 to be retained about a belt, strap, etc. associated with the user, if desired. Thus, it should be understood that the pump clip 100 is not limited to use just with belts or straps associated with a user. The second side 264 also has a recess 278 which is adjacent to the first leaf 250 of the second spring 130. The second spring 130 is in compression in the assembly when the clip 134 is in the first, clamped position.

Figure 11:
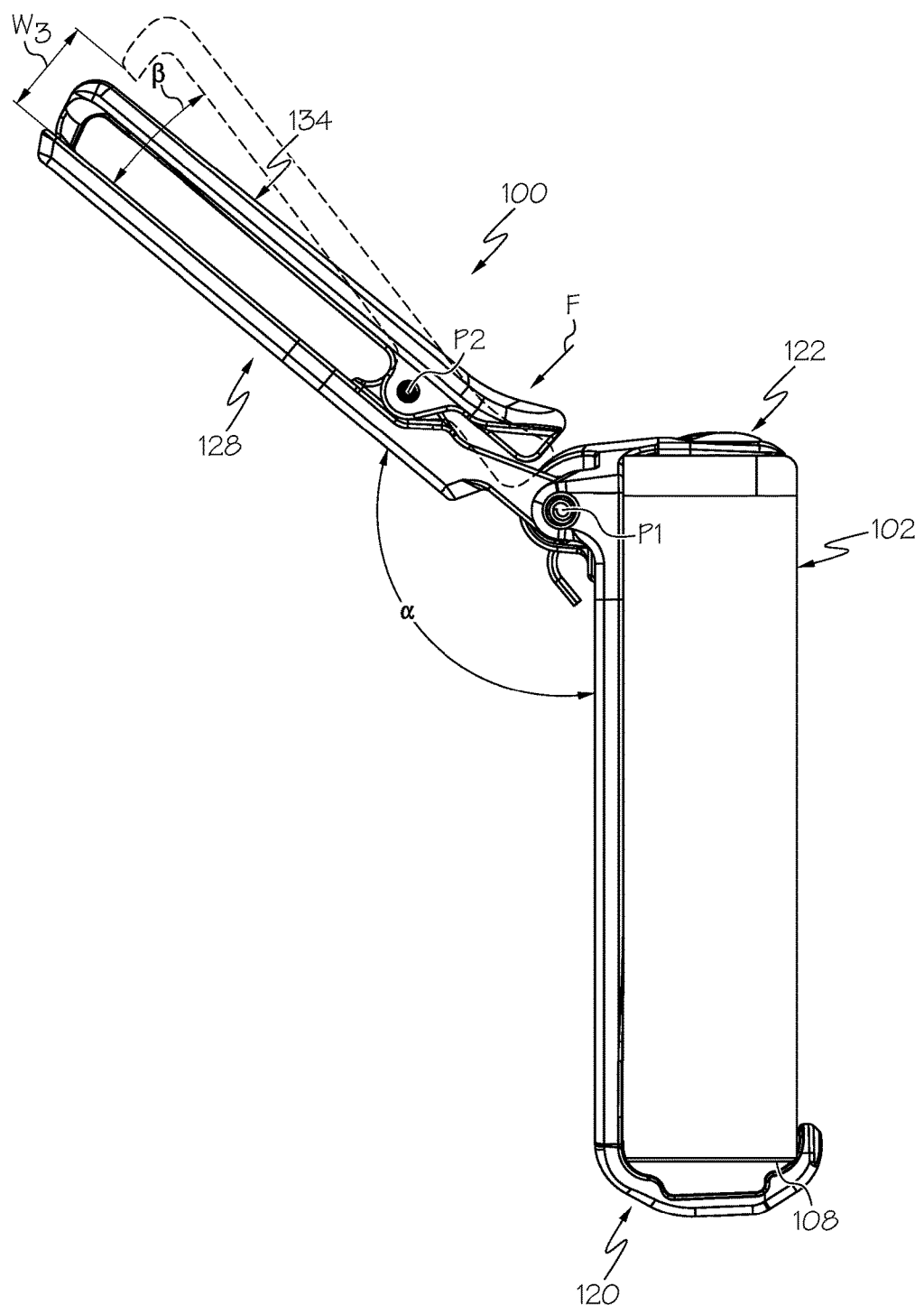
FIG. 11 is a side view of the pump clip and the fluid infusion device of FIG. 1, which illustrates the clip base of the pump clip in the second position, and schematically illustrates the clip in the second position.

With reference to FIG. 11, when a force F is applied to the first end 266 of the clip 134 exceeds the spring force from second spring 130, the clip 134 rotates about the second pivot axis P2 defined by the clamp pin 132 and the second end 268 of the clip 134 is moved to the second, release position in which the clip 134 is open relative to the clip pivot base 128. A width W3 of the opening is at least about 0.4 inches (in.) wide for easy attachment and detachment of the pump clip 100. Although not shown in FIG. 11, the clip pivot base 128 remains engaged with the clip base 120 when operating the clip 134 due to the first spring torque from the first spring 124, and due to the application of the force to the clip 134 between the clamp pin 132 and the hinge pin 126 a moment is only created about the clamp pin 132.

In one example, with reference to FIG. 3, in order to assemble the pump clip 100, with each of the clip base 120, the lock button 122, the first spring 124, the hinge pin 126, the clip pivot base 128, the second spring 130, the clamp pin 132 and the clip 134 formed, the clip pivot base 128 may be positioned within the aperture 148. With the first spring 124 received within the spring cover 154, the first spring leg 200 of the first spring 124 may be positioned within the pivot spring guide 206, and the second spring leg 202 may be positioned within the spring guide 156. With the first pivot bore 232 and the second pivot bore 244 of the clip pivot base 128 coaxially aligned with the internal passage of the 204a of the helical coil body 204, the first bore 150a of the first pin post 150 and the second bore 152a of the second pin post 152, the hinge pin 126 may be inserted through the first pin post 150 and through to the second pin post 152 to couple the clip pivot base 128 to the clip base 120. The spring bore 256 of the second spring 130 may be coupled to the spring retainer 224 to couple the second spring 130 to the clip pivot base 128. The clip hinge projections 272 may be positioned over the respective flange relief 236 such that the clip bores 274, the first clip bore 234 and the second clip bore 246 are coaxially aligned. The clamp pin 132 is inserted through the clip hinge projections 272 such that the clamp pin 132 passes between the first leaf 250 and the second leaf 252 of the second spring 130 to couple the clip 134 to the clip pivot base 128. The lock button 122 may be inserted into the coupling bore 166 of the coupling flange 164.

With the pump clip 100 assembled, the pump clip 100 may be coupled to the fluid infusion device 102. In one example, with reference to FIG. 9A, the pump clip 100 is shown in hands 280 of a user. In this example, an implement 282 is inserted into the key slot 186 and rotated in a counterclockwise direction to move the lock button 122 from the lock position to the unlock position. In the unlock position, the pump clip 100 is capable of being coupled to the fluid infusion device 102, as shown in FIG. 9B. In FIG. 9B, the coupling portion 174 is coupled about the second end 108 of the fluid infusion device 102.

With the coupling portion 174 positioned about the second end 108 of the fluid infusion device 102, with reference to FIG. 9C, the coupling flange 164 may be positioned over the first end 106 of the fluid infusion device 102. The coupling flange 164 is advanced in the slot 110 until the second base side 164 contacts the housing 104 of the fluid infusion device 102. In this position, the lock button 122 is positioned over the protrusion 112 defined on the housing 104. With reference to FIG. 9D, with the pump clip 100 positioned about the fluid infusion device 102, the implement 282 is re-inserted into the key slot 186 and rotated in a clockwise direction to move the lock button 122 from the unlock position to the lock position. In the lock position, the pump clip 100 is securely coupled to the fluid infusion device 102.

With the pump clip 100 securely coupled to the fluid infusion device 102, the pump clip 100 may be used to couple the fluid infusion device 102 to an article or object associated with the user. For example, with reference to FIG. 9E, the pump clip 100 is shown with a belt 284 received within the slot 260 defined between the clip 134 and the primary surface S of the clip pivot base 128. In order to couple the belt 284 to the pump clip 100, the user may apply a force F to the clip 134 to compress the second spring 130 and move the clip 134 to the second, release position. In this regard, the second spring 130 applies a second spring force FS2 that acts against the clip 134 to maintain the clip 134 in the first, clamp position. Once the second spring force FS2 is less than the force F, the clip 134 moves toward the second, release position. In the second, release position, the belt 284 may be positioned between the clip 134 and the clip pivot base 128. Once the belt 284 is positioned between the clip 134 and the clip pivot base 128, the user may remove the force F from the clip 134, which causes the second spring 130 to move the clip 134 from the second, release position to the first, clamp position.

Figure 10:
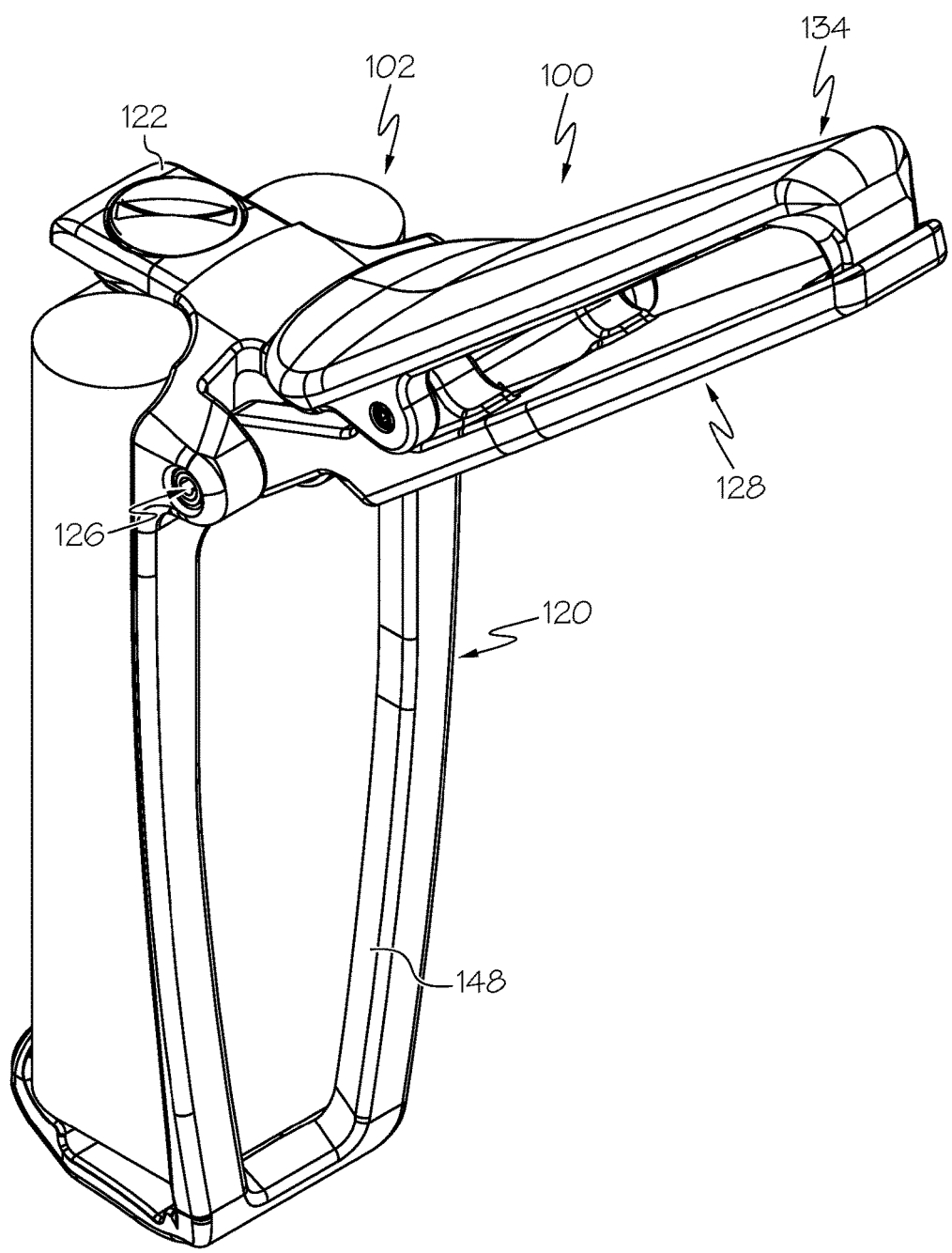
FIG. 10 is a perspective view of the pump clip and fluid infusion device of FIG. 1, which illustrates the clip base of the pump clip in a second position.

With the pump clip 100 and the fluid infusion device 102 coupled to the belt 284, the clip base 120 is movable relative to the clip pivot base 128 to compensate for torques or forces encountered by the fluid infusion device 102. In one example, if the fluid infusion device 102 encounters the torque TE, due to the fluid infusion device 102 contacting a seat belt, arm of a chair, door knob, a torque applied by a user, etc., the first spring 124 resists the torque TE until the torque TE overcomes the first spring torque FS1 of the first spring 124. Once the torque TE is greater than the first spring torque FS1, the clip base 120 moves or pivots from the first position (FIG. 9E), toward the second position as shown in FIG. 10 or to a position between the first position and the second position. With reference to FIG. 10, in the second position, the clip base 120 is rotated about the hinge pin 126 away from the clip pivot base 128, which enables the pump clip 100 to absorb the torque TE, without breaking the pump clip 100 and/or damaging the fluid infusion device 102. By absorbing this torque TE, the pump clip 100 also ensures that the infusion set remains coupled to the user. Alternatively, the user may be the source of the torque TE, as the movement of the clip base 120 relative to the clip pivot base 128 enables the user to rotate the fluid infusion device 102 to view a screen of the fluid infusion device 102 without requiring a removal of the pump clip 100 from the belt 284. In addition, the pump clip 100 is capable of withstanding a force of about 125 pound-force (lbf.) applied in the first pivot axis P1 (in an instance where the pump clip 100 is unable to move to the second position) without damaging the pump clip 100 and/or fluid infusion device 102. It should be noted that while the first spring 124 is described herein as being capable of absorbing the torque by moving the clip base 126 away from the clip pivot base 128, the first spring 124 also absorbs forces, which are applied to the fluid infusion device 102 at a particular position or distance from the first spring 124. Generally, a force of less than 1.0 pound-force (lbf.) acting upward on the fluid infusion device 102 can cause the clip pivot base 128 to rotate to deflect the force.

With reference to FIG. 11, in the second position, the clip base 120 is pivoted along the first pivot axis P1 to an angle α, which in one example, is about 170 degrees to about 180 degrees. In this example, the angle α is about 180 degrees. The angle α represents a maximum angular displacement of the clip base 120 relative to the clip pivot base 128. It should be understood that the clip base 120 may pivot to various other positions between the angle α and the first position (FIGS. 2 and 9E), depending upon an amount of the torque TE (FIG. 9E).

Thus, with reference to FIG. 11, a pivotal movement of the clip base 120 about the first pivot axis P1 defined by the hinge pin 126 occurs when the first spring torque of the first spring 124 is overcome by the torque TE. The first spring torque of the first spring 124 is predetermined such that when the fluid infusion device 102 and/or pump clip 100 experiences the torque TE via pulling, snagging, bumping, etc., while the user is wearing the fluid infusion device 102 with the pump clip 100, the fluid infusion device 102 and the clip base 120 rotate about the first pivot axis P1 defined by the hinge pin 126, which dissipates the energy from pulling, snagging, bumping, etc., so that it prevents damage to the pump clip 100 and/or the fluid infusion device 102. Since the clip base 120 is mounted on the fluid infusion device 102 and the second spring 130 still holds the clip 134 in the first, clamped position onto the clip pivot base 128, the fluid infusion device 102 remains attached to the user's clothing when the first spring torque of the first spring 124 is less than the torque TE during the pulling, snagging, bumping, etc. The first spring 124 returns the pump clip 100 to the first position once the torque TE is removed.

In addition, as shown in FIG. 11, the clip 134 is movable or pivotable about the second pivot axis P2 to an angle β based on an application of the force F (FIG. 9E) to the first end 266 of the clip 134, which in one example, may range from about 10 degrees to about 45 degrees. In this example, the angle β is about 16 degrees. The angle β represents an angular displacement of the clip 134 relative to the clip pivot base 128. It should be understood that the clip 134 may pivot to various other positions between the maximum of the angle β of about 45 degrees and the first position (FIGS. 2 and 9E), depending upon an amount of the force F applied by the user (FIG. 9E).

Figure 12:
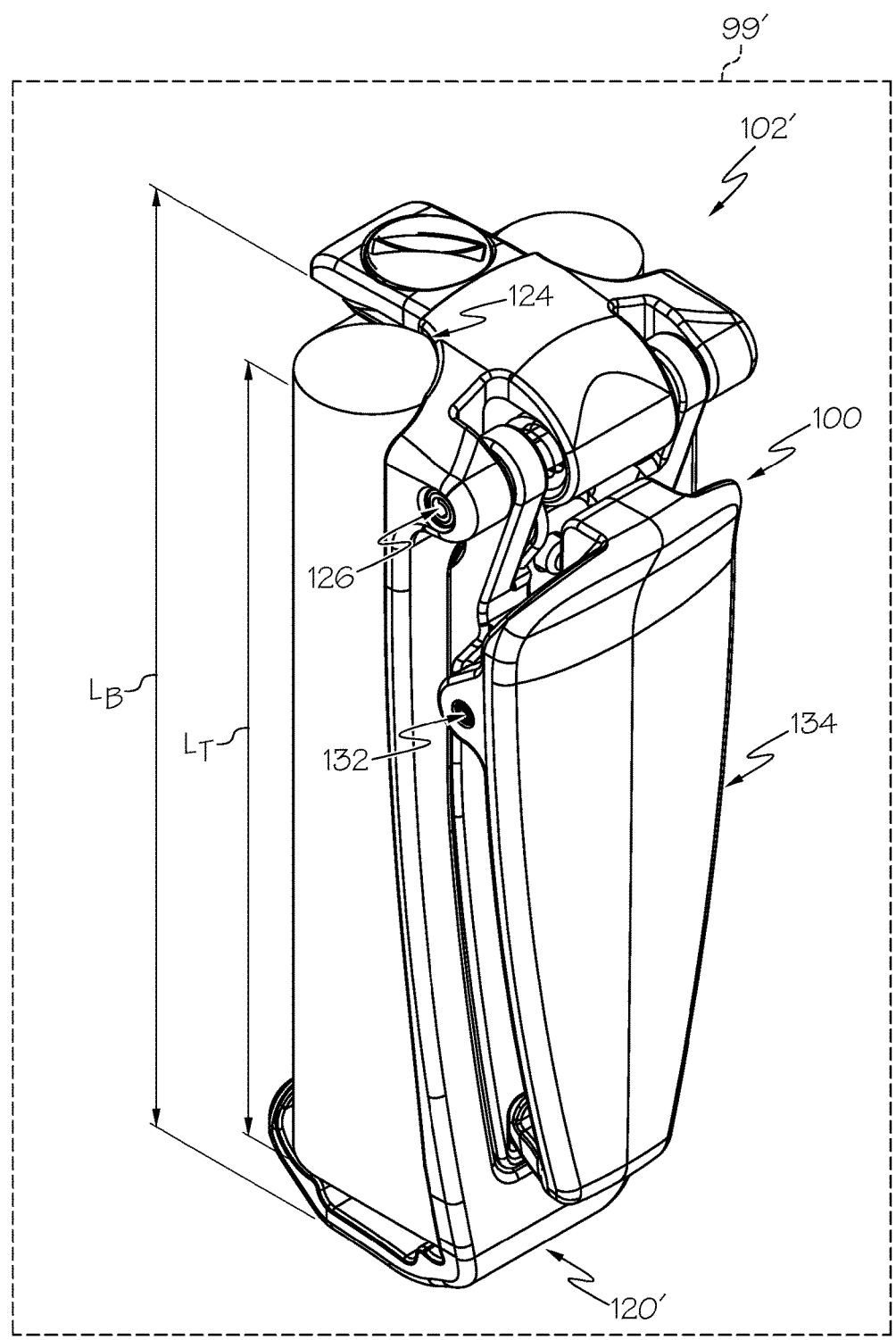
FIG. 12 is a perspective view of another exemplary pump clip for an exemplary fluid infusion device according to various teachings of the present disclosure.

It should be appreciated that the pump clip 100 may be constructed somewhat differently. With reference to FIG. 12, a pump clip 100' is shown. As this pump clip 100' is substantially similar to the pump clip 100 discussed with regard to FIGS. 1-11, the same reference numerals will be used to denote the same or similar components. As shown in FIG. 12, the pump clip 100' is coupled to a fluid infusion device 102'. The pump clip 100' and the fluid infusion device 102' cooperate to define a portable fluid infusion device system 99'. The fluid infusion device 102' may be any fluid infusion device known in the art, and thus, the fluid infusion device 102' will not be discussed in great detail herein. Generally, the fluid infusion device 102' is designed to be carried or worn by the user, and to be coupled to the user via the pump clip 100'. In one example, the fluid infusion device 102' is an insulin infusion device, such as the MiniMed Paradigm® 700 series Insulin Pump, which is commercially available from Medtronic MiniMed, Inc. of Northridge, Calif. The fluid infusion device 102' may leverage a number of conventional features, components, elements, and characteristics described in U.S. Pat. Nos. 6,485,465 and 7,621,893, the relevant content of which is incorporated by reference herein.

Briefly, the fluid infusion device 102' includes a housing 104', which has a length LT, which is greater than a length LT1 of the fluid infusion device 102 (FIG. 1). Thus, the pump clip 100' has a length LB, which is greater than a length LB1 of the pump clip 100 (FIG. 1). The housing 104' has the first end 106 and the second end 108. The first end 106 and the second end 108 are received within a portion of the pump clip 100'.

Figure 13:
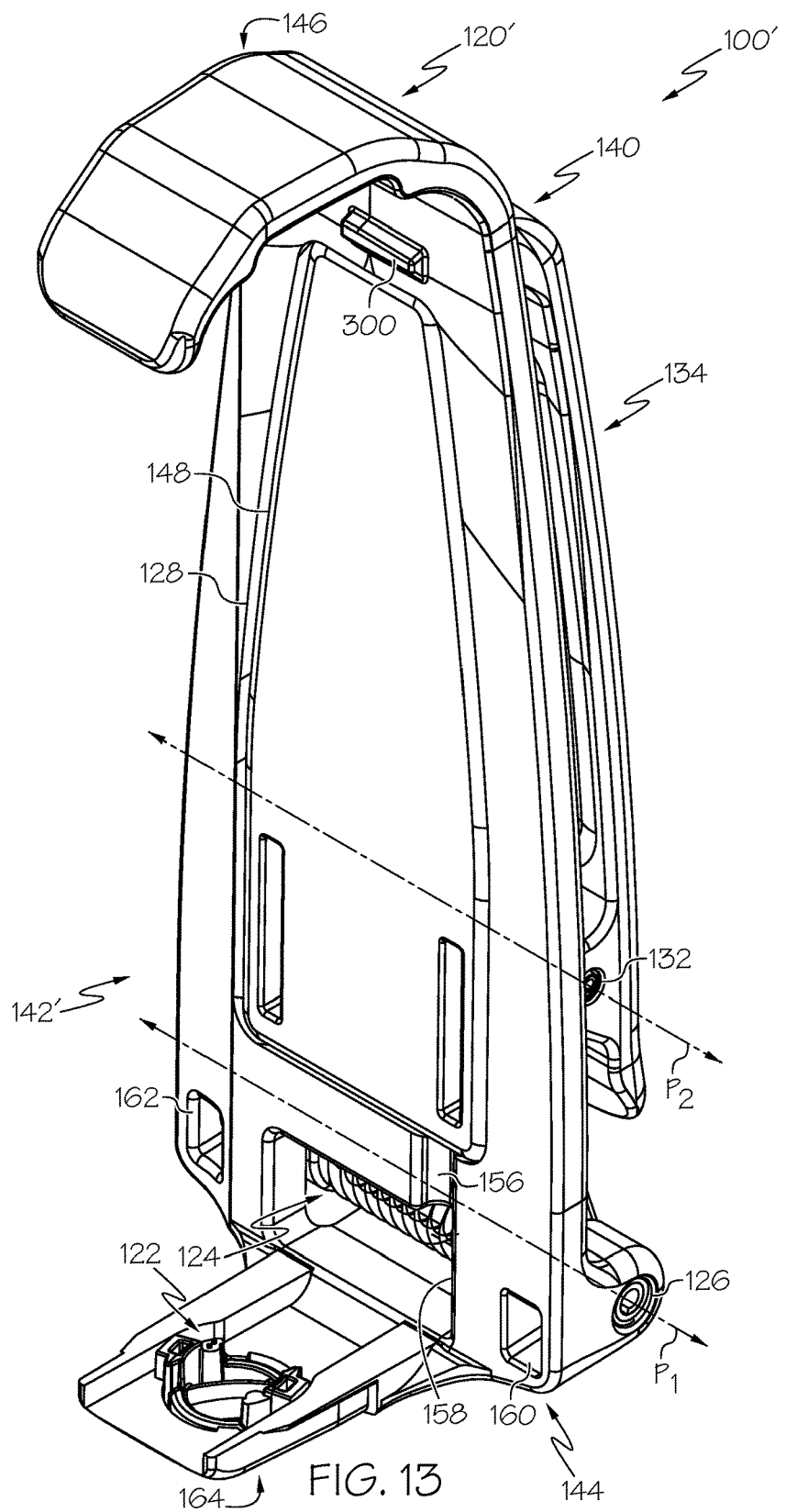
FIG. 13 is a rear perspective view of the pump clip of FIG. 12.

The pump clip 100' includes a clip base 120', the lock button 122, the first spring 124, the hinge pin 126, the clip pivot base 128, the second spring 130, the clamp pin 132 and the clip 134. With reference to FIG. 13, the pump clip 100' is shown detached from the fluid infusion device 102'. As shown, the clip base 120' is configured to receive the fluid infusion device 102'. The clip base 120' includes the first base side 140 opposite a second base side 142', the first base end 144 opposite the second base end 146 and the aperture 148. The clip base 120' is generally composed of a biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. In one example, the clip base 120' is composed of Tritan® COPOLYESTER MX711. The clip base 120' may be formed using casting, printing, molding or another suitable technique.

The second base side 142' is shown in greater detail. The second base side 142 is substantially flat or planar for being positioned against the fluid infusion device 102' (FIG. 12) when the fluid infusion device 102' is coupled to the pump clip 100. The second base side 142' includes the spring guide 156, the spring recess 158, the first relief 160, the second relief 162 and a projection 300. The projection 300 cooperates with the housing 104' to further secure the fluid infusion device 102' to the pump clip 100'. In this example, the projection 300 is received within a recess defined in the housing 104' of the fluid infusion device 102' and cooperates with the recess to prevent the second base end 146 of the clip base 120' from sliding side to side on the fluid infusion device 102'.

As the pump clip 100' is assembled the same way as the pump clip 100, the assembly of the pump clip 100' will not be discussed in great detail herein. Moreover, as the pump clip 100' is coupled to the fluid infusion device 102' in the same manner that the fluid infusion device 102 is coupled to the pump clip 100 as described with regard to FIGS. 9A-9E, the coupling of the fluid infusion device 102' to the pump clip 100' will not be discussed in detail herein. With the pump clip 100' coupled to the fluid infusion device 102', the clip pivot base 128 is pivotable along the first pivot axis P1 to the angle α to absorb the torque TE (the same as that shown with regard to the pump clip 100 of FIGS. 9E and 11). In addition, the clip 134 is movable or pivotable about the second pivot axis P2 to the angle β upon the application of a force to the first end 266 of the clip 134 (the same as that shown with regard to the pump clip 100 of FIG. 11).

Figure 14:
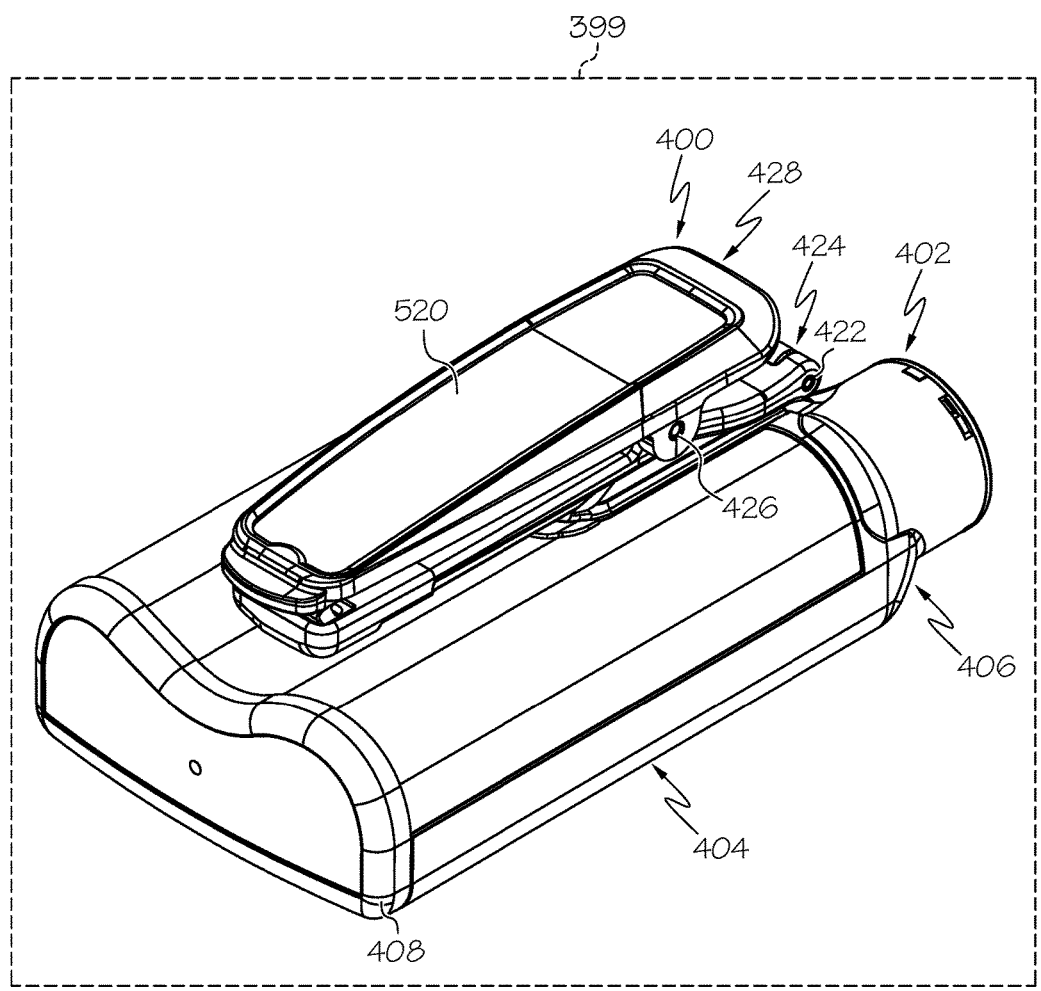
FIG. 14 is a perspective view of another exemplary pump clip for another exemplary fluid infusion device according to various teachings of the present disclosure.

It should be appreciated that the pump clip 100 may be constructed somewhat differently, for use for a different type of fluid infusion device, for example. With reference to FIG. 14, a flip pump clip or pump clip 400 is shown. As this pump clip 400 is similar to the pump clip 100 discussed with regard to FIGS. 1-11, the same reference numerals will be used to denote the same or similar components. As shown in FIG. 14, the pump clip 400 is coupled to a fluid infusion device 402. The pump clip 400 and the fluid infusion device 402 cooperate to define a portable fluid infusion device system 399. The fluid infusion device 402 may be any fluid infusion device known in the art, and thus, the fluid infusion device 402 will not be discussed in great detail herein. Generally, the fluid infusion device 402 is designed to be carried or worn by the user, and to be coupled to the user via the pump clip 400. In one example, the fluid infusion device 402 is an insulin infusion device, such as the MiniMed NGP series Insulin Pump, which is commercially available from Medtronic MiniMed, Inc. of Northridge, Calif. The fluid infusion device 402 may leverage a number of conventional features, components, elements, and characteristics described in U.S. Pat. Nos. 6,485,465 and 7,621,893, the relevant content of which is incorporated by reference herein.

Figure 15:
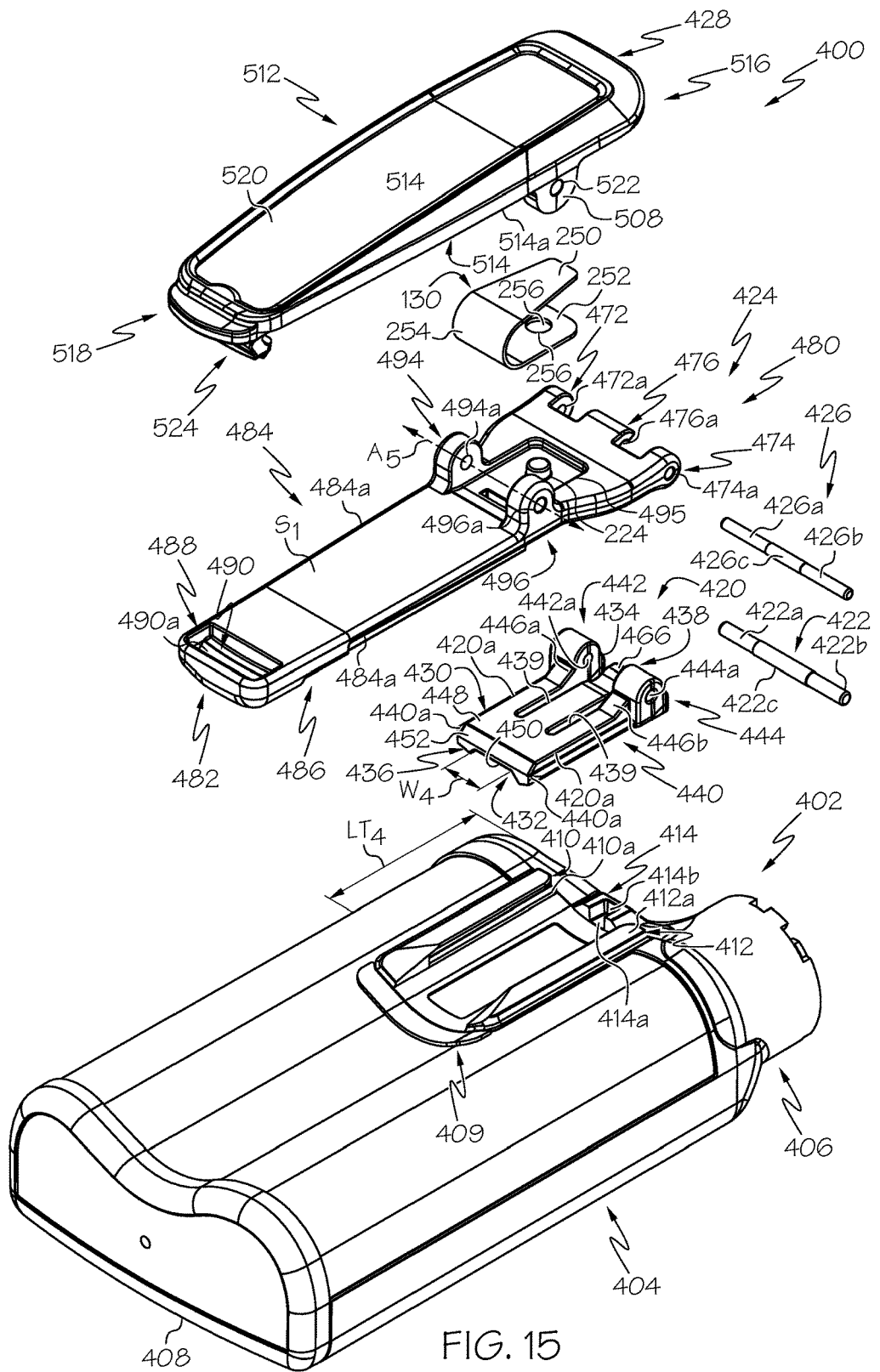
FIG. 15 is an exploded view of the pump clip of FIG. 14, which also illustrates the pump clip exploded from a housing of the fluid infusion device of FIG. 14.

Briefly, the fluid infusion device 402 includes a housing 404. The housing 104 has a first end 406 and an opposite second end 408. With reference to FIG. 15, the first end 406 defines a pump clip plate 409, which includes a first rail 410, a second rail 412 and a knob or notch 414. The first rail 410 and the second rail 412 cooperate to form a pocket that receives a portion of the pump clip 400 to couple the pump clip 400 to the fluid infusion device 402. In one example, the first rail 410 is opposite the second rail 412, and each of the first rail 410 and the second rail 412 define a respective slot 410a, 412a. The slots 410a, 412a slidably receive the portion of the pump clip 400 to couple the pump clip 400 to the fluid infusion device 402. In this example, the slots 410a, 412a extend for a length LT4, however, the first rail 410 and the second rail 412 may have any length that is suitable for receiving the portion of the pump clip 400 to couple the pump clip 400 to the housing 404. The notch 414 provides tactile and audible feedback to the user that the pump clip 400 is coupled to the fluid infusion device 402. The notch 414 is substantially U-shaped, and defines a notch recess 414a. The notch recess 414a includes a stop surface 414b that contacts a portion of the pump clip 400 to provide tactile and audible feedback to the user.

Figure 16:
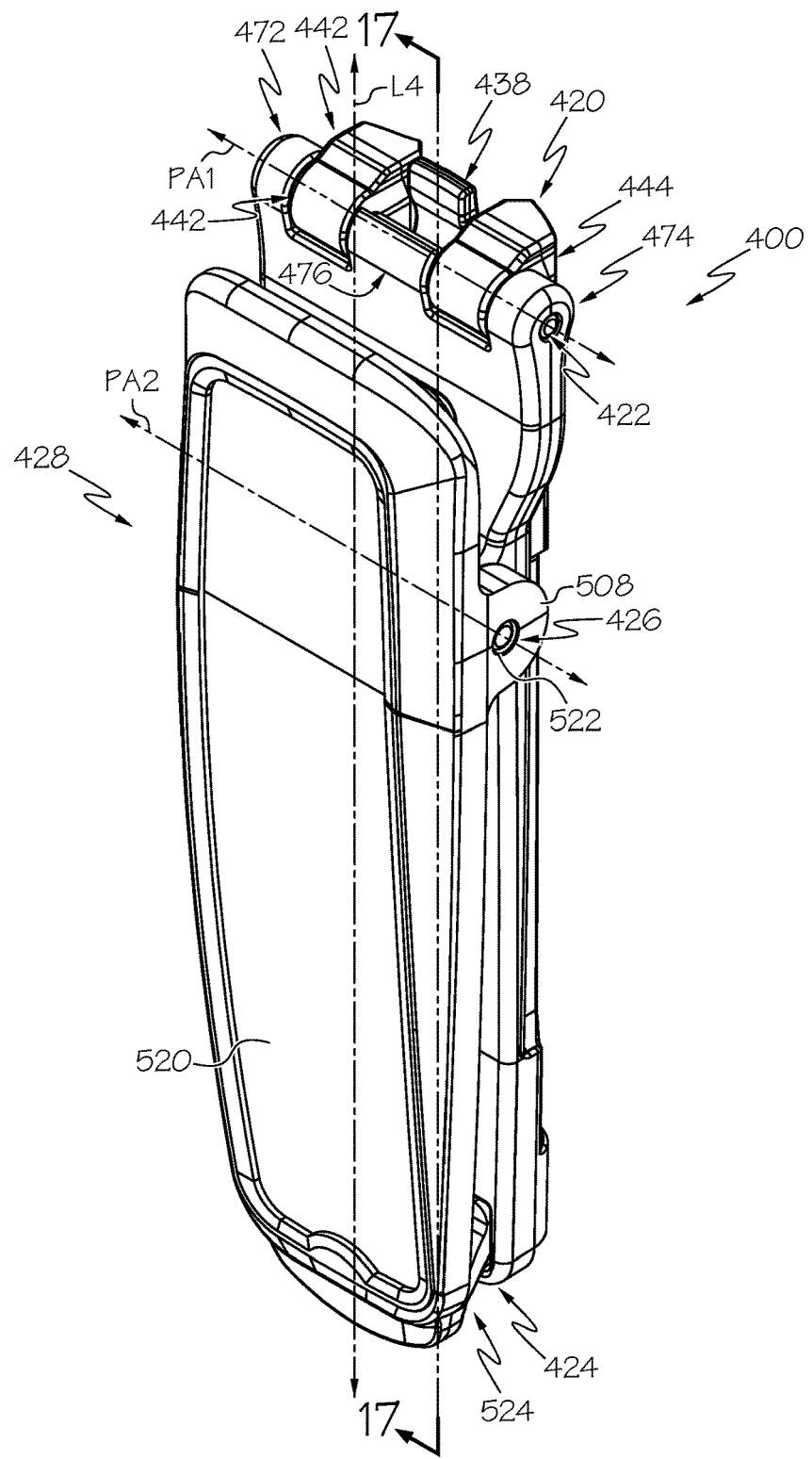
FIG. 16 is a perspective view of the pump clip of FIG. 14.

With reference to FIG. 16, the pump clip 400 is shown detached from the fluid infusion device 402. The pump clip 400 includes a mount 420, a hinge pin 422, a base 424, a clamp pin 426, the second spring 130 (FIG. 15) and a clip 428. With reference back to FIG. 15, the mount 420 couples the pump clip 400 to the fluid infusion device 402. The mount 420 is pivotable along a first pivot axis PA1 defined by the hinge pin 422 between a first position (FIG. 16) and a second position (FIG. 19), and various positions in-between. The mount 420 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The mount 420 may be formed using casting, printing, molding or another suitable technique. The mount 420 includes a first mount side 430 opposite a second mount side 432, a first mount end 434 opposite a second mount end 436, a first lock tab 438 and a pair of opposed wings 440.

The first mount side 430 includes a first mount pin post 442 and a second mount pin post 444 defined at the first mount end 434. The first mount pin post 442 and the second mount pin post 444 each define a respective mount pin bore 442a, 444a, which are coaxially aligned to receive the hinge pin 422. The first mount pin post 442 and the second mount pin post 444 are rounded to provide a smooth surface in case of contact with the user. The first mount side 430 also defines a pair of sloped surfaces 446a, 446b that extend from a respective one of the first mount pin post 442 and the second mount pin post 444 to a planar surface portion 448 of the first mount side 430. The pair of sloped surfaces 446a, 446b re-inforce the first mount pin post 442 and the second mount pin post 444.

The second mount side 432 defines a lip 450 at the second mount end 436. The lip 450 cooperates with a portion of the base 424 via a snap-fit engagement to maintain the base 424 in a first position (FIG. 16). Upon release of the lip 450 by a force, the mount 420 is pivotable about the first pivot axis PA1 defined by the hinge pin 422 to a second position (FIG. 19) and various positions in-between. In one example, a force acting on the fluid infusion device 402 that is greater than about 3 pound-force (lbf.) at the first rail 410 and the second rail 412 of the fluid infusion device 402 causes the release of the lip 450 and the pivoting of the mount 420 about the first pivot axis PA1. Thus, the snap-fit engagement between the lip 450 and the portion of the base 424 remains engaged for forces that are less than about 3 pound-force (lbf.), and the lip 450 disengages from the portion of the base 424 at forces that are greater than about 3 pound-force (lbf.). As shown, in the first position, the mount 420 is adjacent to or next to the base 424, and in the second position, the mount 420 is spaced apart from the base 424. Generally, with reference to FIG. 17, the lip 450 is defined by a relief on the second mount side 432 that extends inwardly from the second mount side 432 to receive a portion of the base 424. With reference back to FIG. 15, in one example, the lip 450 has a width W4 that is configured to withstand a predetermined amount of force before disengaging with the base 424 to enable the mount 420 to move toward the second position (FIG. 19).

Figure 19:
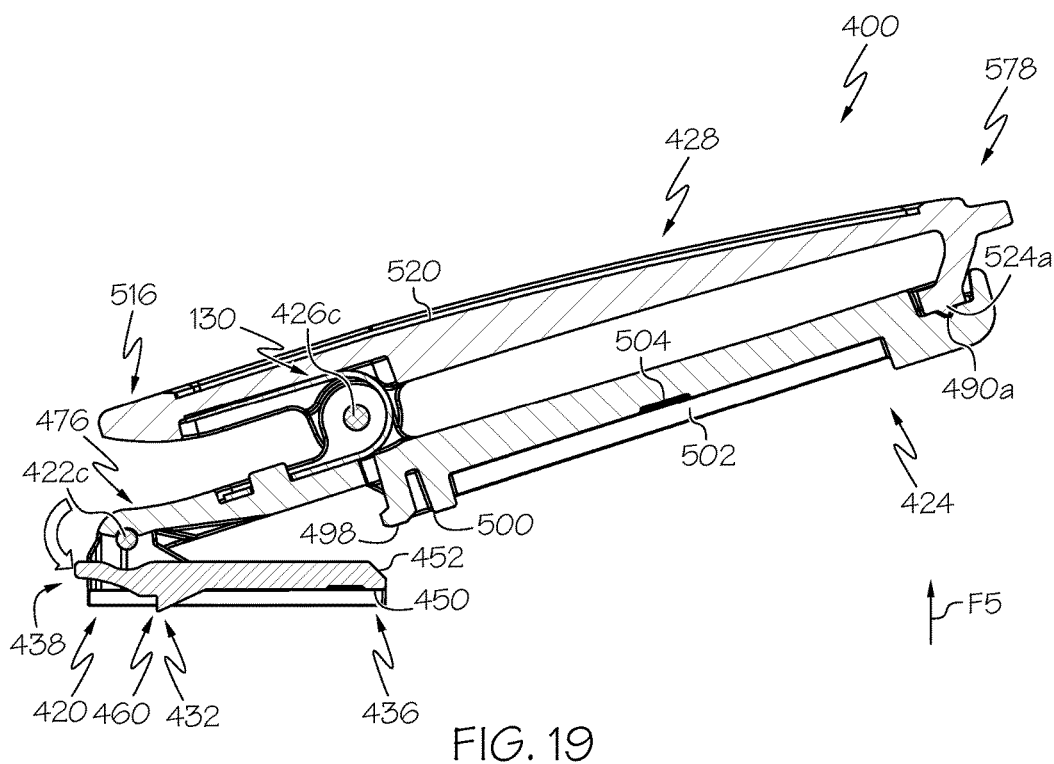
FIG. 19 is a cross-sectional view of the pump clip of FIG. 14, taken from the perspective of line 17-17 of FIG. 16, which illustrates the clip of the pump clip in the first, clamped position and the mount of the pump clip in a second position.
Figure 20:
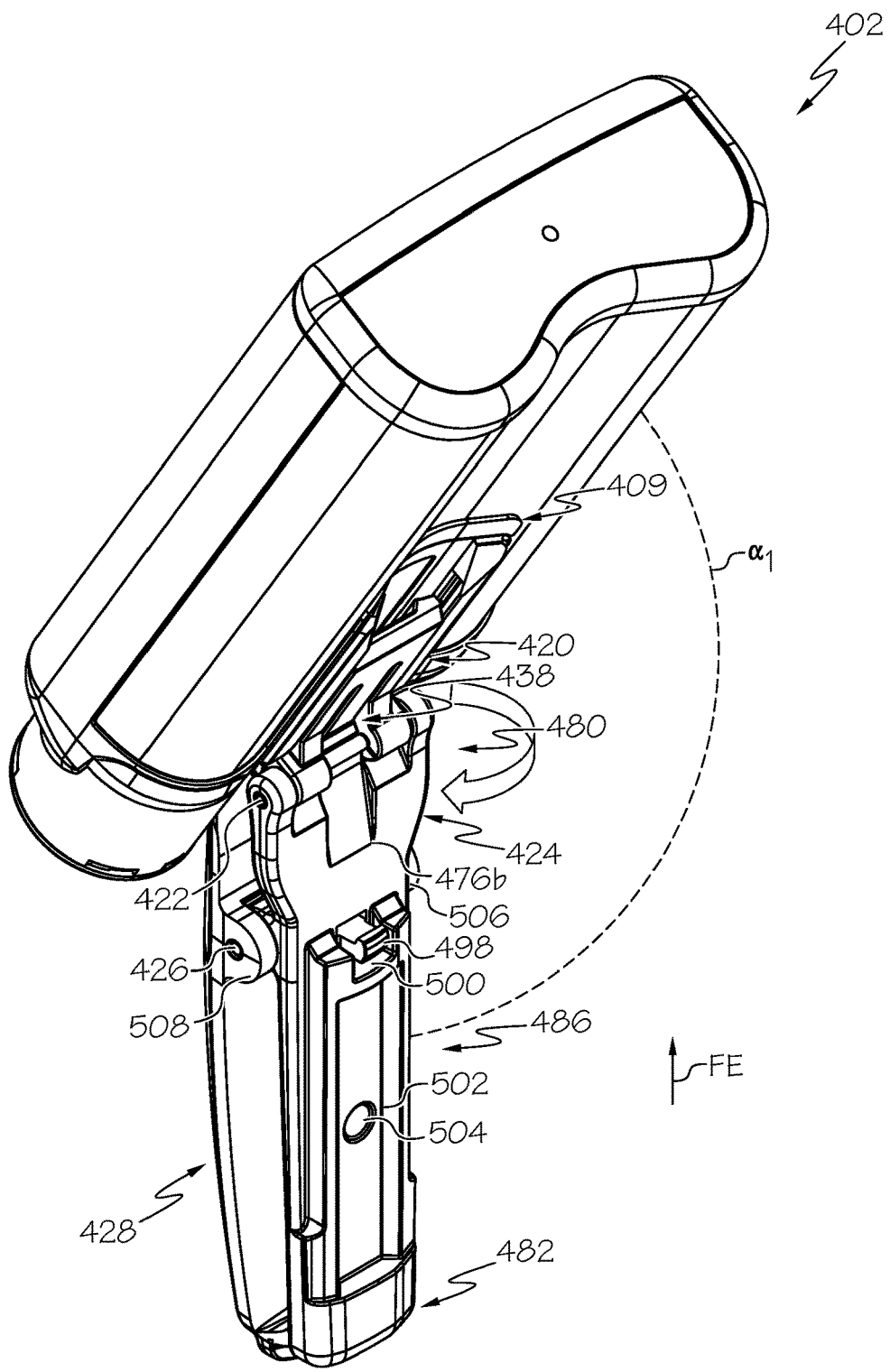
FIG. 20 is a perspective view of the pump clip and the fluid infusion device of FIG. 14, which illustrates the mount of the pump clip in the second position and the clip in the first, clamped position.
Figure 21:
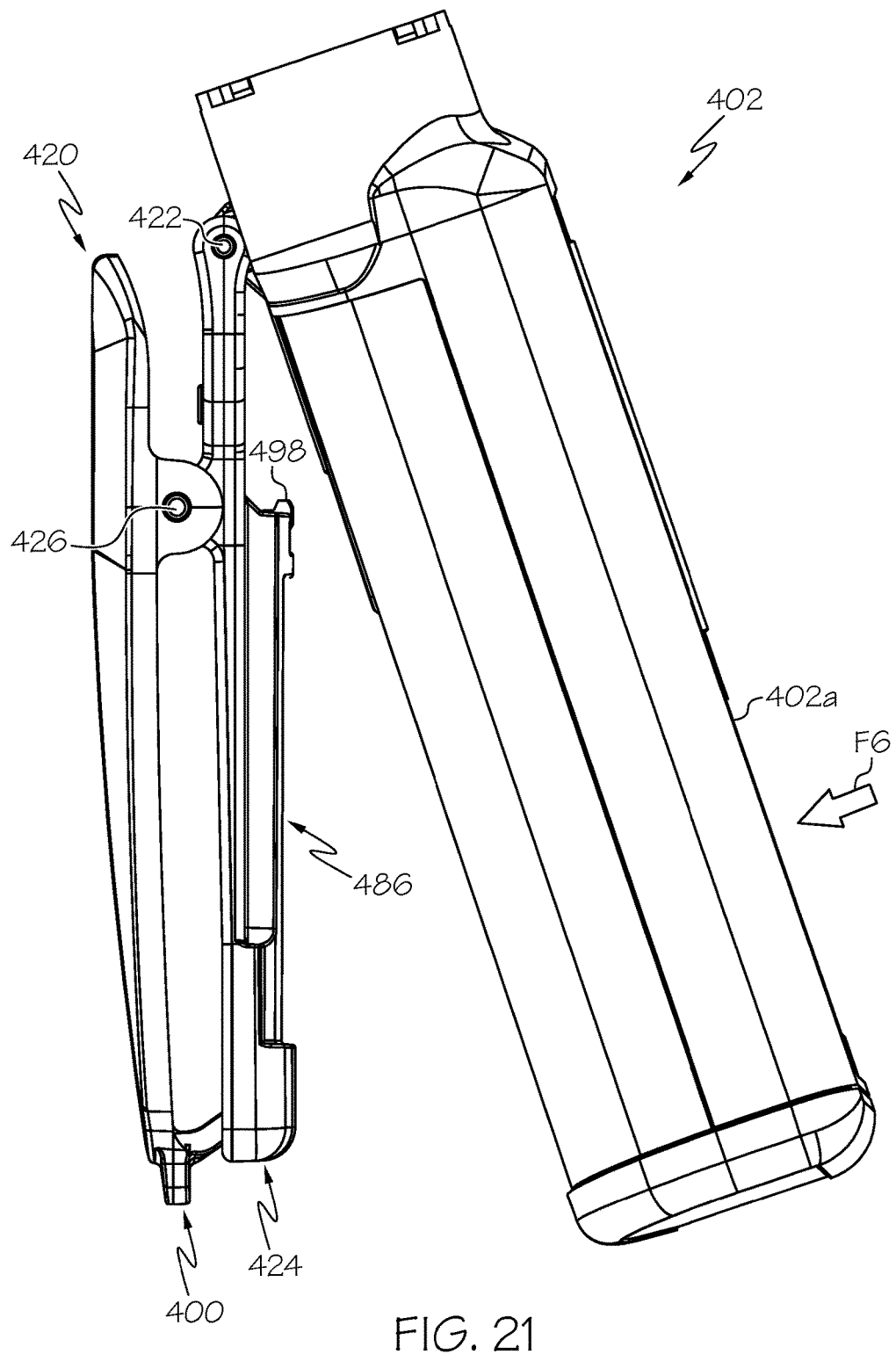
FIG. 21 is a side perspective view of the pump clip and the fluid infusion device of FIG. 14, which illustrates how to move the mount of the pump clip from the second position to the first position in accordance with various embodiments.

In this regard, with reference to FIG. 19, a pivotal movement of the base 424 and the clip 428 against the mount 420 about the first pivot axis PA1 defined by the hinge pin 422 occurs when the lip 450 disengages from the base 424. The lip 450 disengages when the fluid infusion device 402 and/or pump clip 400 experiences a force F5 via pulling, snagging, bumping, or a force applied by the user to view a screen of the fluid infusion device 402, etc., that is greater than about 3 pound-force (lbf.) while the user is wearing the fluid infusion device 402 with the pump clip 400. Once the lip 450 disengages, the fluid infusion device 402 and the mount 420 rotates about the first pivot axis PA1 defined by the hinge pin 422 (See FIG. 20) which dissipates the energy from pulling, snagging, bumping, etc., so that it prevents damage to the pump clip 400 and/or pump clip plate 409 of the fluid infusion device 402. Since the mount 420 is mounted on the fluid infusion device 402 and the second spring 130 still holds the clip 428 in the first, clamped position onto the base 424, the fluid infusion device 402 remains attached to the user's clothing when the lip 450 disengages under the force during pulling, snagging, bumping, etc. With reference to FIG. 21, the pump clip 400 can return to the first position prior to the application of the force by applying a force F6 the fluid infusion device 402 on a front surface 402a of the fluid infusion device 402 to engage the lip 450 to a second lock tab 498 of the base 424 (See FIG. 21).

With reference back to FIG. 15, the second mount end 436 may also define a ramp surface 452 along a width of the second mount end 436. The ramp surface 452 facilitates the engagement of the lip 450 with the portion of the base 424. Generally, as will be discussed further herein, a movement of the first lock tab 438 toward the fluid infusion device 402 (FIG. 14) engages the lip 450 with the base 424, and a movement of the first lock tab 438 away from the fluid infusion device 402 releases the lip 450 from the base 424. Thus, the mount 420 and the base 424 are held together by the engagement of the lip 450 with the base 424.

The first lock tab 438 extends beyond the first mount end 434, and cooperates with the pump clip plate 409 to releasably couple the pump clip 400 to the fluid infusion device 402. In addition, the first lock tab 438 cooperates with the notch 414 (FIG. 14) to provide tactile and audible feedback to the user that the pump clip 400 is coupled to the fluid infusion device 402. In one example, the first lock tab 438 is defined on the mount 420 so as to be cantilevered with regard to the mount 420. In this example, two channels 439 are defined through the first mount side 432 and the second mount side 434 on opposite sides of the first lock tab 438 to enable the first lock tab 438 to move or flex between a first, engaged position (FIG. 17) and a second, disengaged position (FIG. 19) to enable the user to couple the pump clip to the fluid infusion device 402 in the first, engaged position and to uncouple the pump clip 400 from the fluid infusion device 402 in the second, disengaged position.

Figure 17:
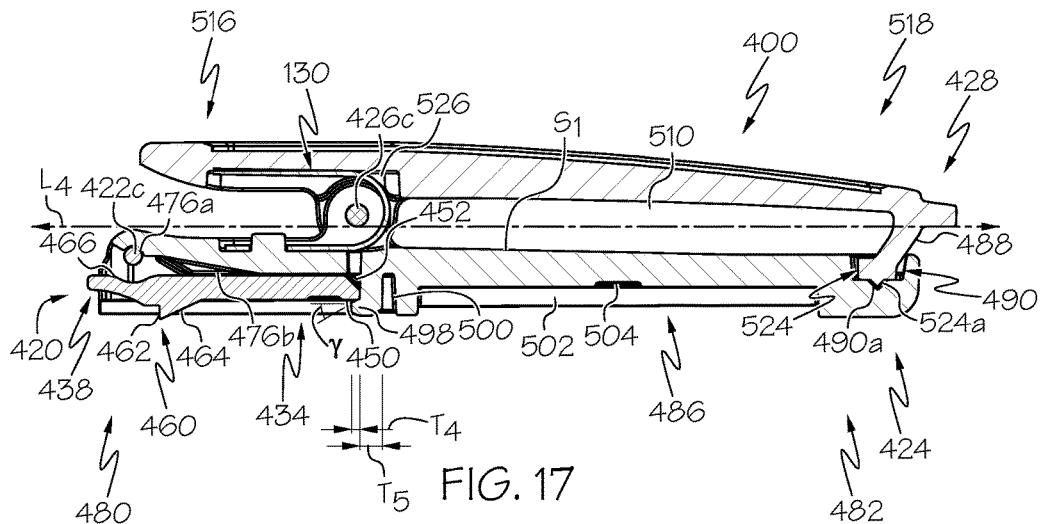
FIG. 17 is a cross-sectional view of the pump clip of FIG. 14, taken along line 17-17 of FIG. 16, which illustrates a clip of the pump clip in a first, clamped position and a mount of the pump clip in a first position.

With reference to FIG. 17, the first lock tab 438 includes a snap fit feature 460, which engages with the notch 414 of the fluid infusion device 402 via a snap-fit engagement in the first, engaged position. The snap fit feature 460, in one example, is a projection, which extends outwardly from the first lock tab 438 on the second mount side 434. The snap fit feature 460 includes a stop or planar surface 462 and an inclined surface 464. The planar surface 462 extends along an axis substantially perpendicular to a longitudinal axis L4 of the pump clip 400. The planar surface 462 abuts against the stop surface 414b of the notch 414 (FIG. 14) when the pump clip 400 is assembled to the fluid infusion device 402 and provides the tactile and audible feedback to the user. The inclined surface 464 guides the first lock tab 438 into the notch 414. The first lock tab 438 also includes a graspable portion 466. The graspable portion 466 provides a contact surface for the user to remove or uncouple the pump clip 400 from the fluid infusion device 402, as will be discussed further herein.

With reference to FIG. 15, the pair of opposed wings 440 are received within a respective one of the slots 410a, 412a to couple the pump clip 400 to the fluid infusion device 402. It should be noted that the wings 440 are identical, and generally, the mount 420 is symmetric about the longitudinal axis L4 (FIG. 17) of the pump clip 400. Each of the wings 440 is substantially flat or planar. Each of the wings 440 extend outwardly from the mount 420 along opposed sidewalls 420a of the mount 420 so as to be defined on the respective sidewall 420a between the first mount side 432 and the second mount side 434. In one example, each of the wings 440 includes a tapered edge 440a, which assists in positioning the wings 440 within the respective one of the slots 410a, 412a.

The hinge pin 422 movably or pivotally couples the base 424 to the mount 420, and defines the first pivot axis PA1 (FIG. 16). The first pivot axis PA1 is substantially perpendicular to the longitudinal axis L4 of the pump clip 400 (FIG. 16). In one example, the hinge pin 422 is a stepped pin, having a diameter at a first end 422a and a second end 422b that is less than a diameter of the hinge pin 422 at a midsection 422c. The stepped diameters along the hinge pin 422 reduces stress on the mount 420 and the base 424, and provide a geometrical interference that assists in retaining the hinge pin 422 within the first mount pin post 442, the second mount pin post 444, and within a portion of the base 424. The hinge pin 422 is composed of a biocompatible metal or metal alloy, such as a stainless steel. The hinge pin 422 may be formed through any suitable technique, such as extrusion, stamping, machining, casting, etc. The first end 422a of the hinge pin 422 is received within a first pivot arm 472 of the base 424 and through the first mount pin post 442; and the second end 422b of the hinge pin 422 is received within a second pivot arm 474 of the base 424 and through the second mount pin post 444. A pivot guide 476 rotates relative to the midsection 422c of the hinge pin 422.

The base 424 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The base 424 may be formed using casting, printing, molding or another suitable technique. The base 424 includes a first base end 480 opposite a second base end 482, and a first base side 484 opposite a second base side 486.

With reference to FIG. 15, the first base end 480 includes the first pivot arm 472, the second pivot arm 474 and the pivot guide 476. The first pivot arm 472, the second pivot arm 474 and the pivot guide 476 are spaced apart along the first base end 480 so that the first mount pin post 442 and the second mount pin post 444 may be received between the first pivot arm 472, the second pivot arm 474 and the pivot guide 476. In one example, the first mount pin post 442 is positioned between the first pivot arm 472 and an end of the pivot guide 476; and the second mount pin post 444 is positioned between an opposite end of the pivot guide 476 and the second pivot arm 474. The first pivot arm 472 defines a first pivot bore 472a, which receives the first end 422a of the hinge pin 422. The second pivot arm 474 defines a second pivot bore 474a, which receives the second end 422b of the hinge pin 422. With reference to FIG. 17, the pivot guide 476 defines a concave recess 476a, which further guides the base 424 for rotation about the hinge pin 422. In this example, the concave recess 476a contacts the midsection 422c of the hinge pin 422 for guiding the base 424 in rotation about the hinge pin 422. The pivot guide 476 also defines a sloped surface 476b on the second base side 486. The sloped surface 476b provides clearance for the movement or flexing of the first lock tab 438 during coupling and uncoupling of the pump clip 400 from the fluid infusion device 402. The first pivot arm 472, the second pivot arm 474 and the pivot guide 476 also cooperate to serve as a stop for limiting a rotation of the clip 428 relative to the base 424.

With reference back to FIG. 15, the second base end 482 includes a clip recess 488. The clip recess 488 is defined at or near the second base end 482 and receives a portion of the clip 428. The clip recess 488 cooperates with a portion of the clip 428 to define a tortuous path for clamping the pump clip 400 to an article of clothing, for example. In this example, the clip recess 488 is substantially rectangular; however, the clip recess 488 may have any desired shape. In this example, the clip recess 488 has an enclosed bottom surface 490, however, it should be understood that the clip recess 488 may comprise an aperture, which receives a portion of the clip 428. With reference to FIG. 17, in one example, the bottom surface 490 includes an indentation 490a, which is configured to mate with the portion of the clip 428 to define the tortuous path. In this example, the indentation 490a is triangular in shape; however, the indentation 490a may have any desired shape that cooperates with the portion of the clip 428 to define the tortuous path.

The first base side 484 includes a pocket or recess 495, a first clip pin post 494 and a second clip pin post 496. The first base side 484 also defines a primary surface S1, which is substantially smooth for receiving an article of clothing, belt, strap, etc., associated with the user. The recess 495 is defined on the first base side 484 near the first base end 480 to receive the second spring 130. The spring retainer 224 is defined in the recess 495, and is coupled to the second spring 130 to retain the second spring 130 on the base 424. In this example, an end or the second leaf 252 of the second spring 130 engages the recess 495, or pocket, within the base 424. The recess 495, or pocket together with the post or the spring retainer 224, securely holds the second leaf 252 of the second spring 130.

The first clip pin post 494 and the second clip pin post 496 each extend outwardly and away from the first base side 484. The first clip pin post 494 and the second clip pin post 496 are spaced apart from each other the first base side 484 such that the first clip pin post 494 and the second clip pin post 496 are on opposed sidewalls 484a of the base 424. Generally, the first clip pin post 494 and the second clip pin post 496 are spaced apart to enable the second spring 130 to be received between the first clip pin post 494 and the second clip pin post 496. The first clip pin post 494 defines a first clip bore 494a, and the second clip pin post 496 defines a second clip bore 496a. The first clip bore 494a and the second clip bore 496a are coaxially aligned along axis A5 to receive the clamp pin 426 therethrough to pivotally couple the clip 428 to the base 424. Thus, the stepped hinge pin 422 is used to connect the mount 420 to the base 424 which allows for pivotal movement of the mount 420 relative to the base 424. The stepped hinge pin 422 is inserted through the pair of mount pin bores 442a, 444a of the first mount pin post 442 and the second mount pin post 444 of the opposed sidewalls 420a of the mount 420 and the pair of openings (first pivot bore 472a and second pivot bore 474a) of the first pivot arm 472 and the second pivot arm 474 of the opposed sidewalls 484a of the base 424.

With reference to FIG. 17, the second base side 486 defines the second lock tab 498, a slot 500 and an elongated recess 502. The second lock tab 498 cooperates with the lip 450. In this regard, in the lock position, the lip 450 is received on or rests on the second lock tab 498. In the unlock position, the lip 450 no longer contacts or is released from the engagement with the second lock tab 498 (FIG. 19). Generally, a thickness T4 of the second lock tab 498 provides an interference onto which the lip 450 is received.

In one example, the thickness T4 is between about 0.01 inches (in.) to about 0.05 inches (in.). An angle γ is the snap-fit angle between the lip 450 and the second lock tab 498. In one example, the angle γ is about 20 degrees to about 85 degrees. A thickness T5 of the second lock tab 498 is about 0.05 inches (in.) to about 0.125 inches (in.). Each of the thickness T4, the thickness T5 and the angle γ cooperate to determine the amount of force the mount 420 may withstand before moving toward the second position (FIG. 19). In one example, the mount 420 may withstand a force of 3 pound-force (lbf.) before the snap-fit between the lip 450 and the second lock tab 498 is released and the mount 420 moves toward the second position.

The slot 500 enables the second lock tab 498 to move or flex to release the lip 450. The slot 500 may be defined between the second lock tab 498 and the elongated recess 502. With reference to FIG. 20, the elongated recess 502 may defined through a portion of the second base side 486 near or adjacent to the slot 500, and may extend from near or adjacent to the slot 500 to near or adjacent to the second base end 482. The elongated recess 502 provides a mass savings. A bore 504 is defined through the elongated recess 502, which assists in the formation of the base 424 via injection molding, for example. It should be noted that the bore 504 may be optional.

The clamp pin 426 movably or pivotally couples the clip 428 to the base 424, and defines a second pivot axis PA2 (FIG. 16). The second pivot axis PA2 is substantially perpendicular to the longitudinal axis L4 of the pump clip 400 (FIG. 16), and is substantially parallel to the first pivot axis PA1. Generally, the second pivot axis PA2 is offset from or spaced apart from the first pivot axis PA1 along the longitudinal axis L4 of the pump clip 400. In one example, the clamp pin 426 is a stepped pin, having a diameter at a first end 426a and a second end 426b that is less than a diameter of the clamp pin 426 at a midsection 426c. The stepped diameters along the clamp pin 426 reduces stress on the base 424 and the clip 428, and provide a geometrical interference that assists in retaining the clamp pin 426 within the first clip pin post 494, the second clip pin post 496, and within a portion of the clip 428. The clamp pin 426 is composed of a biocompatible metal or metal alloy, such as a stainless steel. The clamp pin 426 may be formed through any suitable technique, such as extrusion, stamping, machining, casting, etc. The first end 426a of the clamp pin 426 is received within a first clip projection 506 (FIG. 20) of the clip 428 and through the first clip pin post 494; and the second end 426b of the clamp pin 426 is received within a second clip projection 508 of the clip 428 and through the second clip pin post 496. The midsection 426c of the clamp pin 426 is received through the second spring 130.

The second spring 130 (FIG. 15) is coupled to the base 424. The first leaf 250 is compressible by a force applied to the clip 428 to move the clip 428 from a first, clamped position to a second, release position. Thus, in this example, the second spring 130 is a leaf spring that is adapted to hold the clip 428 a closed position onto the base 424 and provide desired clip force to attach to a user. The spring bore 256 of the second leaf 252 receives the spring retainer 224 therethrough to couple the second spring 130 to the base 424. The body 254 couples the first leaf 250 to the second leaf 252, and provides a second spring force that maintains the clip 428 in the first, clamped position.

The clip 428 cooperates with the primary surface S1 of the base 424 to define a slot, generally indicated by reference numeral 510 in FIG. 17, for receipt of an article of clothing or item associated with the user, such as a shirt, belt, strap, etc. when the clip 428 is in the first, clamped position. The clip 428 is composed of a biocompatible polymeric material, including, but not limited to copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The clip 428 may be formed using casting, printing, molding or another suitable technique. The clip 428 includes a first side 512 opposite a second side 514, and a first end 516 opposite a second end 518.

The first side 512 is substantially smooth, and includes a recessed surface 520 that extends from the first end 516 to the second end 518. The recessed surface 520 provides a location for a removable graphical and/or textual indicator, such as a sticker, decal or decorative skin, which enables the user to personalize the pump clip 400. The second side 514 is substantially smooth, and includes the first clip projection 506 and the second clip projection 508, which extend outwardly from the second side 512 near the first end 516. The first clip projection 506 and the second clip projection 508 are spaced apart from each other on opposed sidewalls 514a of the clip 428 on the second side 514. In this example, each of the first clip projection 506 and the second clip projection 508 includes a clip bore 522, which receives a respective first end 426a and second end 426b of the clamp pin 426. Thus, the clip 428 is rotatably mounted to the base 424 by the stepped clamp pin 426 inserted through the pair of the clip bores 522 of the first clip projection 506 and the second clip projection 508 that extend from opposed sidewalls 514a of the clip 428 and the pair of the clip bores 494a, 496a of the first clip pin post 494 and the second clip pin post 496, respectively, on the opposed sidewalls 484a of the base 424.

The second side 514 also includes a hook or clip projection 524 at the second end 518. With reference to FIG. 17, the clip projection 524 extends outwardly from the second side 264, and is substantially U-shaped. The clip projection 524 cooperates with the clip recess 488 to define a tortuous path for capturing an article of clothing or other item associated with the user to secure the pump clip 400 to the particular article of clothing or other item. In one example, the clip projection 524 includes a protrusion 524a, which extends outwardly and away from a surface of the clip projection 524. In this example, the protrusion 524a is substantially triangular, and is shaped to be received within the indentation 490a of the clip recess 488. The engagement of the protrusion 524a and the indentation 490a assists the pump clip 400 in further clamping or gripping onto an article of clothing or item associated with the user, such as a shirt, belt, strap, etc. Thus, the clip projection 524 enables the clip 428 to clamp onto an article of clothing or other item associated with the user, and the slot 510 also enables the pump clip 400 to be retained about a belt, strap, etc. associated with the user, if desired. Thus, it should be understood that the pump clip 400 is not limited to use just with belts or straps associated with a user. In addition, it should be understood that the clip projection 524 need not include the protrusion 524a, but rather, the clip projection 524 may be rounded similar to the clip projection 276 of the pump clip 100 of FIGS. 1-11, if desired.

Figure 18:
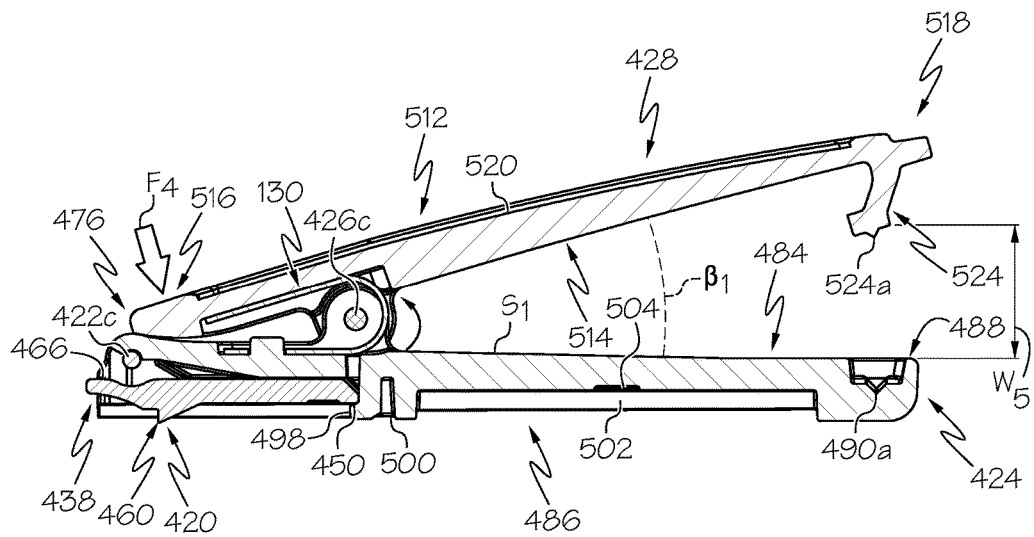
FIG. 18 is a cross-sectional view of the pump clip of FIG. 14, taken from the perspective of line 17-17 of FIG. 16, which illustrates the clip of the pump clip in a second, released position and the mount of the pump clip in the first position.

The second side 514 also has a recess 526 which engages the first leaf 250 of the second spring 130. The second spring 130 is in compression in the assembly when the clip 428 is in the first, clamped position such that in the first, clamped position shown in FIG. 17, the clip projection 524 at the second end of the clip 428 is in compression resting in the clip recess 488 within the base 424, which provides better attachment of the pump clip 400 on the article associated with the user, such as a shirt, belt, strap, etc. With reference to FIG. 18, when a force F4 is applied to the first end 516 of the clip 428 exceeds the spring force from second spring 130, the clip 428 rotates about the second pivot axis PA2 defined by the clamp pin 426 and the second end 518 of the clip 428 is moved to the second, release position in which the clip 428 is open relative to the base 424. A width W5 of the opening is at least about 0.4 inches (in.) wide for easy attachment and detachment of the pump clip 400. The lip 450 remains engaged with the base 424 when operating the clip 428.

In one example, with reference to FIG. 15, in order to assemble the pump clip 400, with each of the mount 420, the hinge pin 422, the base 424, the second spring 130, the clamp pin 426 and the clip 428 formed, the base 424 may be coupled to the mount 420 such that the lip 450 of the mount 420 engages the second lock tab 498 of the base 424. With the first pivot bore 472a and the second pivot bore 474a of the base 424 coaxially aligned with the mount pin bore 442a of the first mount pin post 442 and the mount pin bore 444a of the second mount pin post 444, the hinge pin 422 may be inserted through the first pivot arm 472 and through to the second pivot arm 474 to couple the base 424 to the mount 420. The second spring 130 may be positioned within the recess 495 defined on the first base side 484, and the spring bore 256 of the second spring 130 may be coupled to the spring retainer 224 to couple the second spring 130 to the base 424. The clip bores 522 of the first clip projection 506 and the second clip projection 508 may be positioned over the base 424 such that the clip bores 522, the first clip bore 494a and the second clip bore 496a are coaxially aligned. The clamp pin 426 is inserted through the clip bore 522 of the first clip projection 506, the first clip bore 494a, the second clip bore 496a and the clip bore 522 of the second clip projection 508 such that the clamp pin 426 passes between the first leaf 250 and the second leaf 252 of the second spring 130 to couple the clip 428 to the base 424.

Figure 22:
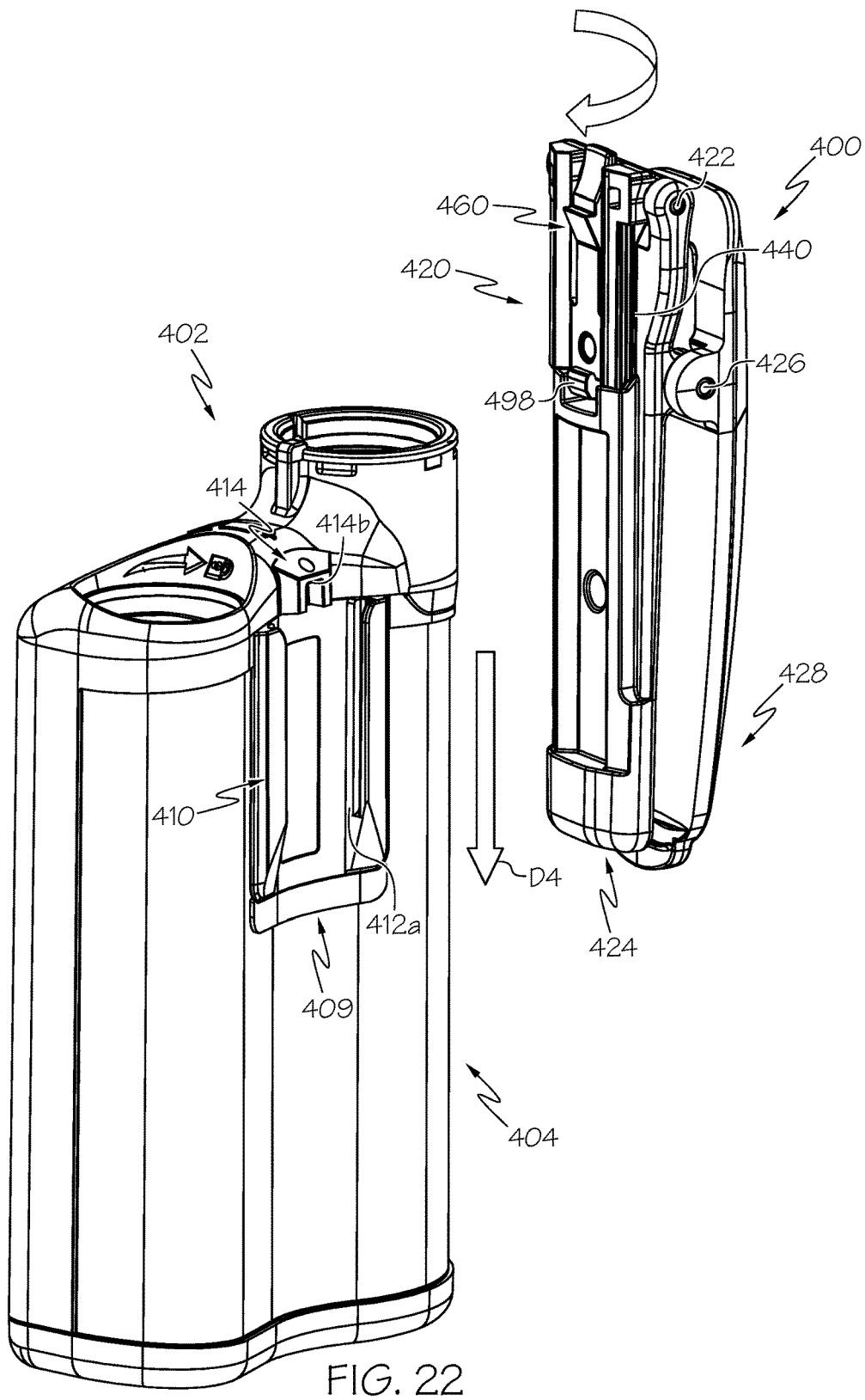
FIG. 22 is a side perspective view of the pump clip and the fluid infusion device of FIG. 14, which illustrates an attachment process for coupling the pump clip to the fluid infusion device in accordance with various embodiments.
Figure 23A:
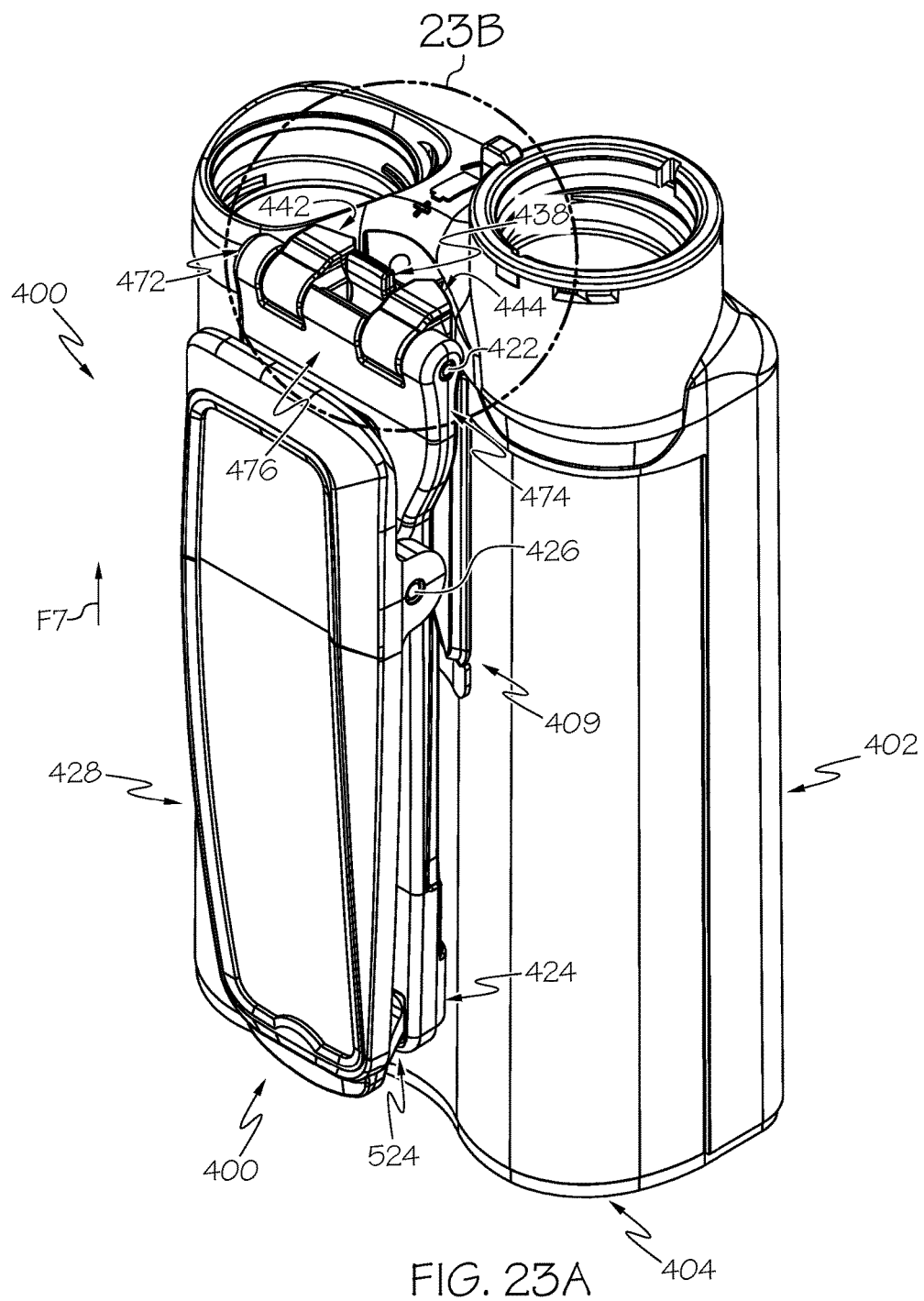
FIG. 23A is a perspective view of the pump clip and the fluid infusion device of FIG. 14, which illustrates a first action to detach the pump clip from the fluid infusion device when the pump clip is fully engaged with the fluid infusion device.

With the pump clip 400 assembled, the pump clip 400 may be coupled to the fluid infusion device 402. In one example, with reference to FIG. 22, with the pump clip plate 409 defined on the fluid infusion device 402, the wings 440 on the mount 420 are aligned with the slots 410a, 412a of the rails 410, 412 on the housing 404. The wings 440 on the mount 420 are inserted into the rails 410, 412, such that the wings 440 slide in a direction D4 along the slots 410a, 412a until the snap fit feature 460 engages the notch 414 on the housing 404 of the fluid infusion device 402. Once the snap fit feature 460 engages, a tactile and audible feedback is provided to the user to indicate the pump clip 400 is fully installed. With reference to FIG. 23A, the pump clip 400 is shown fully installed on the fluid infusion device 402.

With the pump clip 400 fully installed on the fluid infusion device 402, the pump clip 400 and the fluid infusion device 402 may be coupled to user. When coupled to the user, the mount 420 is movable relative to the base 424 to compensate for forces applied to the fluid infusion device 402. In one example, with reference to FIG. 20, if the fluid infusion device 402 encounters a force FE, due to the fluid infusion device 402 encountering a seat belt, arm of a chair, door knob, a force applied by a user, etc., the lip 450 resists the force FE until the force FE overcomes the lip 450 and the lip 450 disengages with the base 424. Once the lip 450 disengages from the base 424, the mount 420 moves or pivots from the first position (FIG. 14), toward the second position as shown in FIG. 20 or to a position between the first position and the second position. In the second position, the mount 420 is rotated about the hinge pin 422 away from the base 424, which enables the pump clip 400 to absorb the force FE, without breaking the pump clip 400 and/or damaging the fluid infusion device 402. By absorbing this force FE, the pump clip 400 also ensures that the infusion set remains coupled to the user. Alternatively, the user may be the source of the force FE, as the movement of the mount 420 relative to the base 424 enables the user to rotate the fluid infusion device 402 to view a screen of the fluid infusion device 402 without requiring a removal of the pump clip 400 from the user.

With reference to FIG. 20, in the second position, the mount 420 is pivoted along the first pivot axis PA1 to an angle α1, which in one example, is about 170 degrees to about 180 degrees. In this example, the angle α1 is about 180 degrees. The angle α1 represents a maximum angular displacement of the mount 420 relative to the base 424. It should be understood that the mount 420 may pivot to various other positions between the angle α1 and the first position (FIGS. 14 and 17), depending upon an amount of the force FE (FIG. 20).

In addition, as shown in FIG. 18, the clip 428 is movable or pivotable about the second pivot axis PA2 to an angle β1 based on an application of the force F to the first end 516 of the clip 428, which in one example, may range from about 10 degrees to about 45 degrees. In this example, the angle β1 is about 17 degrees. The angle β1 represents an angular displacement of the clip 428 relative to the base 424. It should be understood that the clip 428 may pivot to various other positions between the maximum of the angle β1 of about 45 degrees and the first position (FIGS. 14 and 17), depending upon an amount of the force F applied by the user (FIG. 18).

Figure 23B:
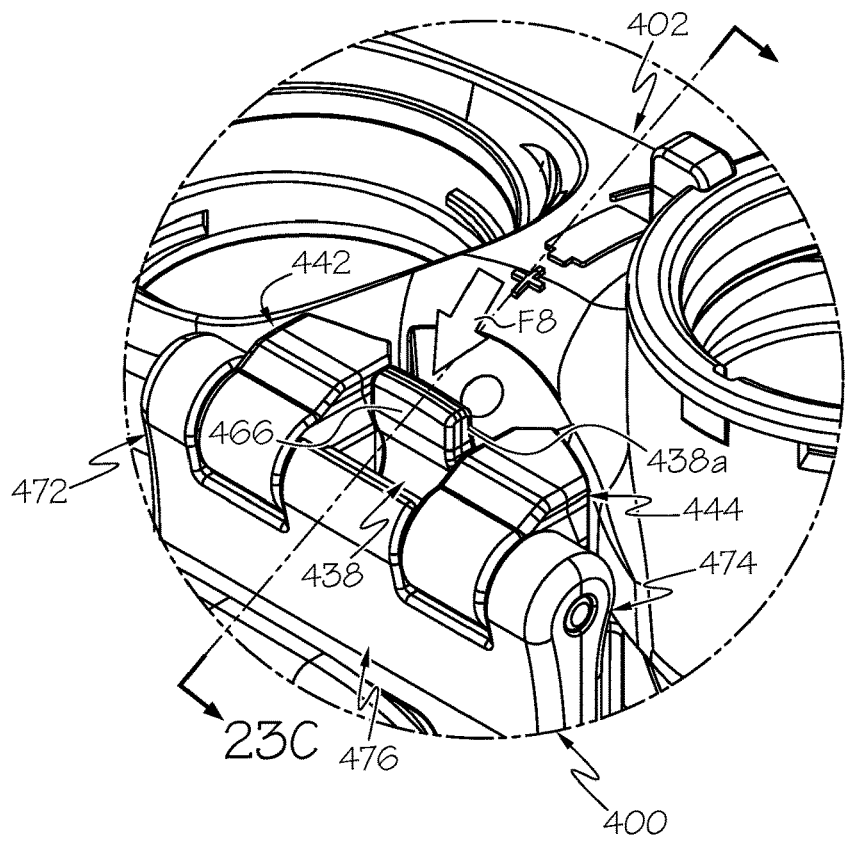
FIG. 23B is a detail perspective view taken at 23B of FIG. 23A, which illustrates a second action to detach the pump clip from the fluid infusion device.
Figure 23C:
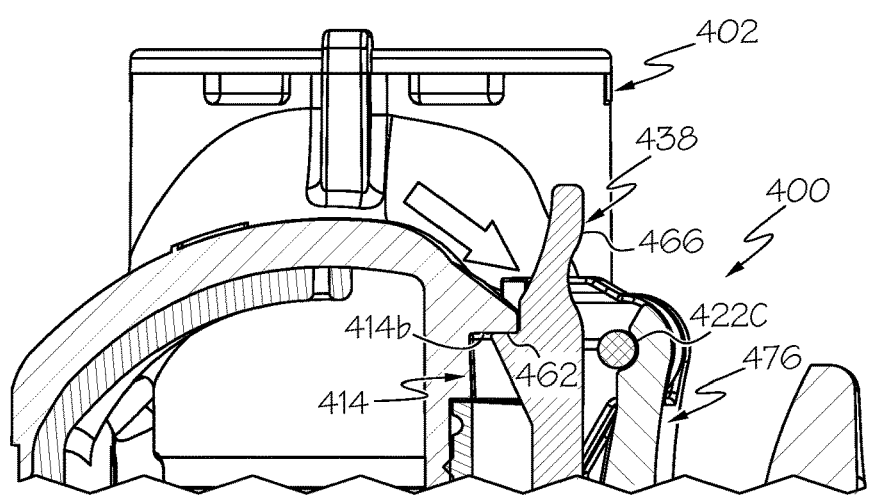
FIG. 23C is a cross-sectional view taken along line 23C-23C of FIG. 23B, which illustrates a third action to detach the pump clip from the fluid infusion device.

In order to remove the pump clip 400 from the fluid infusion device 402, in one example, with reference to FIG. 23A, a force F7 is applied by the user, which lifts up the first lock tab 438. In example, the force F7 is less than about 13.0 pound-force (lbf). With reference to FIGS. 23B and 23C, with the first lock tab 438 lifted up, a force F8 is applied by the user to a rear surface 438a of the first lock tab 438 to disengage the lip 450 with the second lock tab 498 of the base 424. Once the lip 450 is disengaged, the pump clip 400 may be moved in the direction of the force F7 (FIG. 23A) to slide the wings 440 toward the notch 414. Once the wings 440 are removed or disengaged with the slots 410a, 412a of the rails 410, 412, the pump clip 400 is uncoupled or removed from the fluid infusion device 402.

Thus, the pump clips 100, 100', 400 each securely couple the respective fluid infusion device 102, 402 to the user and absorb torques or forces acting on the respective fluid infusion device 102, 402, such as those encountered during an accidental displacement of the respective fluid infusion device 102, 402 or during a user's rotation of the fluid infusion device 102, 402 to view a screen associated with the fluid infusion device 102, 402, etc. In this regard, the rotation of the clip base 120 enables the respective pump clip 100, 100' to absorb the torque without damaging the pump clip 100, 100' and/or the respective fluid infusion device 102. The rotation of the mount 420 enables the pump clip 400 to absorb the force without damaging the pump clip 400 and/or the respective fluid infusion device 402. Moreover, by composing the pump clips 100, 100', 400 of copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate; and metal or metal alloy, the pump clips 100, 100', 400 are resistant to exposure to chemicals, such as sun screen, body lotion, finger oils, and detergents, which prolongs a useful life of the pump clips 100, 100', 400. Further, the smooth first side 262 of the clip 134 and the smooth first side 512 of the clip 428 provide comfort to the user during extended periods of wear.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A portable fluid infusion device system, comprising:
   a fluid infusion device having a pump clip interface that defines a pair of rails; and
   a pump clip coupled to the pump clip interface, the pump clip including:
   a mount that includes wings defined on opposed sides of the mount, each of the wings received within a respective one of the pair of rails to position the pump clip on the fluid infusion device, a first lock tab cantilevered and movable relative to the mount to couple the pump clip to the fluid infusion device and a lip, the mount having a first mount end opposite a second mount end, with the first lock tab extending beyond the first mount end and the lip defined at the second mount end;
   a base coupled to the mount that defines a second lock tab that engages with the lip to retain the mount in a first position, the mount pivotable about a first pivot axis into a second position in which the mount is spaced apart from the base; and
   a clip coupled to the base, the clip pivotable about a second pivot axis relative to the base between a first, clamped position and a second, released position to receive an article.

2. The portable fluid infusion device system of claim 1, wherein the mount is pivotable from the first position to the second position based on a disengagement of the second lock tab and the lip.

3. The portable fluid infusion device system of claim 1, wherein the base defines a recess on a first base side, and the pump clip further comprises a leaf spring retained in the recess and coupled to the base, the leaf spring biases the clip in the first, clamped position.

4. The portable fluid infusion device system of claim 1, further comprising a stepped hinge pin, and the hinge pin is coupled to the mount and the base to define the first pivot axis.

5. The portable fluid infusion device system of claim 1, further comprising a stepped clamp pin, and the clamp pin is coupled to the base and the clip to define the second pivot axis.

6. The portable fluid infusion device system of claim 1, wherein the clip includes a first end opposite a second end, and the second end includes a clip projection that includes a protrusion that mates with the base to define a tortuous path.

7. The portable fluid infusion device system of claim 6, wherein the base has a first base end opposite a second base end, and the second base end defines a clip recess that includes an indentation that mates with the protrusion of the clip projection to define the tortuous path.

8. The portable fluid infusion device system of claim 1, wherein the mount has a first mount side opposite a second mount side, and the first lock tab includes a snap fit feature that extends outwardly from the second mount side to engage with the fluid infusion device.

9. A portable fluid infusion device system, comprising:
a fluid infusion device having a pump clip interface that defines a pair of rails; and
a pump clip coupled to the pump clip interface, the pump clip including:
a mount that includes wings defined on opposed sidewalls of the mount, a first lock tab and a lip, each of the wings received within a respective one of the pair of rails to position the pump clip on the fluid infusion device and the first lock tab is cantilevered and is movable relative to the pump clip interface between a first, engaged position in which the first lock tab cooperates with the pump clip interface to couple the pump clip to the fluid infusion device and a second, disengaged position;
a base coupled to the mount that defines a second lock tab that engages with the lip to retain the mount in a first position, the mount pivotable about a first pivot axis into a second position in which the mount is spaced apart from the base; and
a clip coupled to the base and the clip is pivotable about a second pivot axis relative to the base between a first, clamped position and a second, released position to receive an article.

10. The portable fluid infusion device system of claim 9, wherein based on a disengagement of the second lock tab and the lip, the mount pivots from the first position to the second position.

11. The portable fluid infusion device system of claim 9, wherein the base defines a recess on a first base side, and the pump clip further comprises a leaf spring retained in the recess and coupled to the base, the leaf spring biases the clip in the first, clamped position.

12. The portable fluid infusion device system of claim 9, further comprising a stepped hinge pin, and the hinge pin is coupled to the mount and the base to define the first pivot axis.

13. The portable fluid infusion device system of claim 9, further comprising a stepped clamp pin, and the clamp pin is coupled to the base and the clip to define the second pivot axis.

14. The portable fluid infusion device system of claim 9, wherein the clip includes a first end opposite a second end, and the second end includes a clip projection that includes a protrusion that mates with the base to define a tortuous path.

15. The portable fluid infusion device system of claim 9, wherein the mount has a first mount side opposite a second mount side and a first mount end opposite a second mount end, with the first lock tab extending beyond the first mount end and the lip defined at the second mount end, the pump clip interface defines a notch, and the first lock tab includes a snap fit feature that extends outwardly from the second mount side that engages with the notch of the pump clip interface of the fluid infusion device to releasably couple the pump clip to the fluid infusion device.

16. The portable fluid infusion device system of claim 9, wherein the fluid infusion device is an insulin infusion device.

17. A portable fluid infusion device system, comprising:
a fluid infusion device having a pump clip interface that defines a pair of rails and a notch; and
a pump clip coupled to the pump clip interface, the pump clip including:
a mount that includes wings defined on opposed sidewalls of the mount, a first lock tab and a lip, each of the wings slidably received within a respective one of the pair of rails to position the pump clip on the fluid infusion device and the first lock tab is cantilevered and movable relative to the notch of the pump clip interface between a first, engaged position in which the first lock tab is engaged with the notch to couple the pump clip to the fluid infusion device and a second, disengaged position;
a base coupled to the mount that defines a second lock tab that snap-fits with the lip to retain the mount in a first position, the mount pivotable about a first pivot axis into a second position in which the mount is spaced apart from the base; and
a clip coupled to the base and the clip is pivotable about a second pivot axis relative to the base between a first, clamped position and a second, released position to receive an article.

18. The portable fluid infusion device system of claim 17, wherein based on a disengagement of the second lock tab and the lip, the mount pivots from the first position to the second position.

19. The portable fluid infusion device system of claim 17, further comprising a stepped hinge pin, and the hinge pin is coupled to the mount and the base to define the first pivot axis.

20. The portable fluid infusion device system of claim 17, further comprising a stepped clamp pin, and the clamp pin is coupled to the base and the clip to define the second pivot axis.

* * * * *